(12) United States Patent
Nikolski et al.

(10) Patent No.: US 12,172,010 B2
(45) Date of Patent: *Dec. 24, 2024

(54) MEDICAL DEVICE AND METHOD FOR GENERATING MODULATED HIGH FREQUENCY ELECTRICAL STIMULATION PULSES

(71) Applicant: Medtronic, Inc., Minneapolis, MN (US)

(72) Inventors: Vladimir P. Nikolski, Blaine, MN (US); Melissa G. T. Christie, Ham Lake, MN (US); Mark T. Marshall, Cape Coral, FL (US); Amy E. Thompson-Nauman, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/324,781

(22) Filed: May 26, 2023

(65) Prior Publication Data
US 2023/0293890 A1 Sep. 21, 2023

Related U.S. Application Data

(63) Continuation of application No. 17/175,806, filed on Feb. 15, 2021, now Pat. No. 11,697,023.
(Continued)

(51) Int. Cl.
*A61N 1/362* (2006.01)
*A61B 5/363* (2021.01)
(Continued)

(52) U.S. Cl.
CPC .............. *A61N 1/36* (2013.01); *A61B 5/363* (2021.01); *A61N 1/362* (2013.01); *A61N 1/3621* (2013.01);
(Continued)

(58) Field of Classification Search
CPC ........ A61N 1/362; A61N 1/36; A61N 1/3621; A61N 1/3712; A61N 1/39622;
(Continued)

(56) References Cited

U.S. PATENT DOCUMENTS 5,282,843 A 2/1994 Freeman
5,480,414 A * 1/1996 Stroebel ............... A61N 1/3712
607/28
(Continued)

FOREIGN PATENT DOCUMENTS

CN 105664356 A 6/2016
WO 2005118063 A1 12/2005
(Continued)

OTHER PUBLICATIONS

Extended European Search Report for EP Application No. 21164617.9 issued on Aug. 17, 2021 (8 pages).

*Primary Examiner* — Catherine M Voorhees

(57) ABSTRACT

A medical device is configured to deliver therapeutic electrical stimulation pulses by generating frequency modulated electrical stimulation pulse signals. The medical device includes a pulse signal source and a modulator. The pulse signal source generates an electrical stimulation pulse signal having a pulse width. The modulator may include a high frequency modulator configured to modulate a frequency of the pulse signal from a starting frequency down to a minimum frequency during the pulse width. The modulator may include a low frequency bias generator to modulate the offset of the pulse signal between a minimum offset and a maximum offset in other examples.

21 Claims, 14 Drawing Sheets

Related U.S. Application Data

(60) Provisional application No. 63/001,812, filed on Mar. 30, 2020.

(51) Int. Cl.
    *A61N 1/36*     (2006.01)
    *A61N 1/37*     (2006.01)
    *A61N 1/39*     (2006.01)

(52) U.S. Cl.
    CPC ....... *A61N 1/3712* (2013.01); *A61N 1/39622* (2017.08)

(58) Field of Classification Search
    CPC ........ A61N 1/371; A61N 1/3981; A61N 1/02; A61N 1/025; A61N 1/0563; A61N 1/057; A61N 1/365; A61N 1/372; A61N 1/37512; A61N 1/37518; A61N 1/3756; A61N 1/3956; A61N 1/3975; A61B 5/363
    See application file for complete search history.

(56) References Cited

U.S. PATENT DOCUMENTS

| | | | |
|---|---|---|---|
| 5,782,882 | A | 7/1998 | Lerman et al. |
| 6,438,418 | B1 | 8/2002 | Swerdlow et al. |
| 6,731,979 | B2 | 5/2004 | MacDonald |
| 7,340,302 | B1 * | 3/2008 | Falkenberg .......... A61N 1/3611 607/9 |
| 8,014,858 | B1 | 9/2011 | Ben-Haim et al. |
| 8,620,428 | B2 | 12/2013 | Hincapie Ordonez et al. |
| 11,697,023 | B2 * | 7/2023 | Nikolski .............. A61N 1/3712 607/4 |
| 2004/0116974 | A1 | 6/2004 | Obel |
| 2006/0155335 | A1 * | 7/2006 | Ohman .............. A61N 1/39622 607/5 |
| 2007/0299895 | A1 * | 12/2007 | Johnson ................ G06F 1/0321 708/270 |
| 2009/0030476 | A1 | 1/2009 | Hargrove |
| 2009/0157131 | A1 | 6/2009 | Ideker et al. |
| 2009/0177110 | A1 | 7/2009 | Lyden et al. |
| 2014/0180355 | A1 * | 6/2014 | Ghosh ................ A61N 1/36842 607/28 |
| 2014/0228837 | A1 | 8/2014 | Giovangrandi et al. |
| 2016/0089540 | A1 | 3/2016 | Bolea |
| 2016/0158567 | A1 | 6/2016 | Marshall et al. |
| 2019/0015671 | A1 | 1/2019 | Anderson et al. |
| 2019/0329041 | A1 * | 10/2019 | Corndorf ........... A61N 1/36153 |
| 2021/0361943 | A1 * | 11/2021 | Black .................... A61N 2/002 |

FOREIGN PATENT DOCUMENTS

| | | |
|---|---|---|
| WO | 2007127592 A1 | 11/2007 |
| WO | 2015102004 A1 | 7/2015 |

* cited by examiner

MEDICAL DEVICE AND METHOD FOR GENERATING MODULATED HIGH FREQUENCY ELECTRICAL STIMULATION PULSES

REFERENCE TO RELATED APPLICATIONS

This application is a continuation of U.S. patent application Ser. No. 17/175,806, filed Feb. 15, 2021, which claims the benefit of and priority to U.S. Provisional Patent Application Ser. No. 63/001,812, filed Mar. 30, 2020, the entire content of both of which is incorporated by reference herein.

TECHNICAL FIELD

The disclosure relates generally to a medical device and method for generating modulated high frequency electrical stimulation pulses.

BACKGROUND

Medical devices may be configured to generate electrical pulses for delivering an electrical stimulation therapy to treat a pathological condition or otherwise alter the state or activity of electrically excitable tissue such as a patient's heart, brain, spinal cord, nerve, skeletal muscle or smooth muscle. Such devices may be implantable, wearable or external devices including or electrically coupled to implantable and/or surface (skin) electrodes for delivering the electrical stimulation pulses. In some cases, the electrical stimulation device may be configured to sense electrophysiological signals from the heart, brain, nerve, muscle or other tissue and deliver the electrical stimulation therapy based on the sensed electrophysiological signals.

For example, implantable or external cardiac pacemakers, cardioverter defibrillators, cardiac monitors and the like, sense cardiac electrical signals from a patient's heart. A cardiac pacemaker or cardioverter defibrillator may deliver therapeutic electrical stimulation to the heart via electrodes carried by one or more medical electrical leads and/or electrodes on a housing of the medical device. The electrical stimulation may include signals such as pacing pulses or cardioversion or defibrillation shocks. In some cases, a medical device may sense cardiac electrical signals attendant to the intrinsic or pacing-evoked depolarizations of the heart and control delivery of stimulation signals to the heart based on sensed cardiac electrical signals. Upon detection of an abnormal rhythm, such as bradycardia, tachycardia or fibrillation, an appropriate electrical stimulation signal or signals may be delivered to restore or maintain a more normal rhythm of the heart. For example, an implantable cardioverter defibrillator (ICD) may deliver pacing pulses to the heart of the patient upon detecting bradycardia or tachycardia or deliver cardioversion or defibrillation (CV/DF) shocks to the heart upon detecting tachycardia or fibrillation.

In some proposed or available ICD systems, an extra-cardiac lead may be coupled to the ICD, in which case delivery of cardiac electrical stimulation pulses from electrodes outside the heart may cause other, non-targeted excitable tissue, such as skeletal muscle or nerves, to be electrically stimulated. This extraneous stimulation may be perceived by the patient and may cause annoyance, discomfort or pain. In other medical devices or medical device systems, electrodes may be located on a surface of a body of the patient, e.g., on a skin of the patient, for delivering electrical stimulation pulses to a targeted nerve, organ, or muscle.

SUMMARY

In general, the disclosure is directed to a medical device and techniques for generating therapeutic electrical stimulation pulses. A medical device operating according to the techniques disclosed herein generates therapeutic electrical stimulation pulse by generating a high frequency electrical stimulation pulse signal that is modulated over the pulse width of the pulse signal. The modulation may include modulation between a maximum frequency and a minimum frequency of the oscillations of the pulse signal during the pulse width. The modulation may additionally or alternatively include modulating the bias of the pulse signal between a minimum offset and a maximum offset in other examples. In some examples, the amplitude of the oscillations of the pulse signal is modulated up to a maximum amplitude, which may coincide in time with the minimum frequency of the oscillations and/or the maximum bias offset in some examples.

In one example, the disclosure provides a medical device having a therapy delivery circuit including a signal source and a modulator. The signal source is configured to generate an electrical stimulation pulse signal having a pulse width. The modulator is configured to modulate the frequency of oscillations of the electrical stimulation pulse signal between a minimum frequency and a maximum frequency during the pulse width and/or modulate the bias of the electrical stimulation pulse signal between a minimum offset and a maximum offset during the pulse width. The modulator may be coupled to an output circuit that is coupleable to an electrical stimulation electrode for delivering the modulated electrical stimulation pulse signal.

In another example, the disclosure provides a method for delivering an electrical stimulation therapy. The method includes generating an electrical stimulation pulse signal having a pulse width and modulating the frequency of oscillations of the electrical stimulation pulse signal between a minimum frequency and a maximum frequency during the pulse width and/or modulating the bias of the electrical stimulation pulse signal between a minimum offset and a maximum offset during the pulse width.

In another example, the disclosure provides a non-transitory computer-readable medium storing a set of instructions which, when executed by a control circuit of a medical device, cause the medical device to deliver an electrical stimulation therapy by generating an electrical stimulation pulse signal having a pulse width and modulating the frequency of oscillations of the electrical stimulation pulse signal between a minimum frequency and a maximum frequency during the pulse width and/or modulating the bias of the electrical stimulation pulse signal between a minimum offset and a maximum offset during the pulse width.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

Figure 1A:
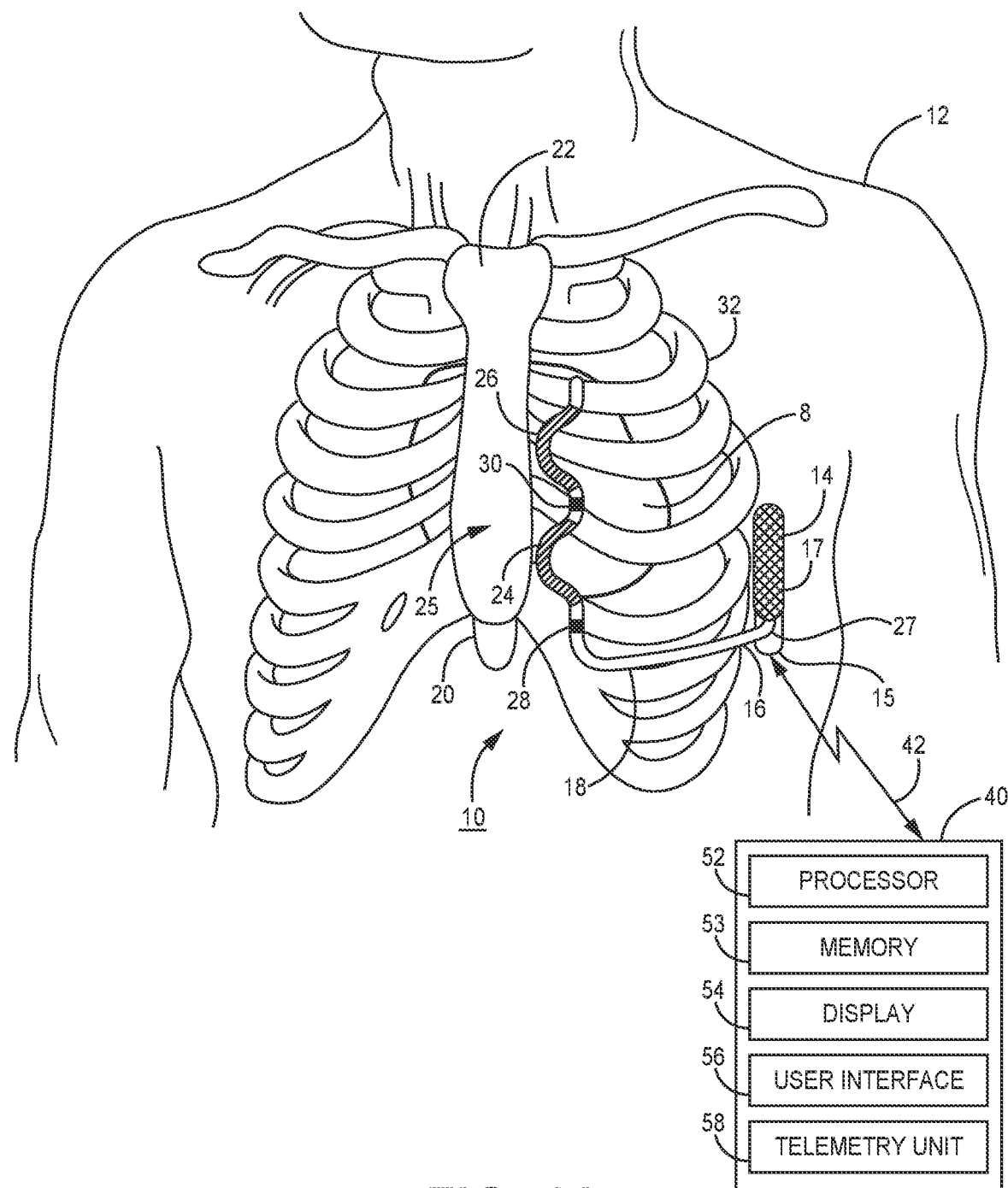
FIGS. 1A and 1B are conceptual diagrams of an extra-cardiovascular ICD system configured to sense cardiac electrical events and deliver cardiac electrical stimulation therapies according to one example.

In general, this disclosure describes techniques for generating and delivering therapeutic electrical stimulation pulses for treating a condition or disease while minimizing patient discomfort or pain caused by extraneous stimulation of non-targeted tissue by the therapeutic electrical stimulation pulses. The techniques disclosed herein may be implemented in a variety of external, wearable or implantable medical devices configured to deliver electrical stimulation pulses to body tissue using external surface (skin) electrodes, transcutaneous electrodes, or implantable electrodes. In some applications, the therapy delivery electrodes may not be in direct contact with the targeted body tissue being stimulated by the therapeutic electrical stimulation pulses. The delivered electrical current may pass through non-targeted tissue, including muscle and nerves, causing extraneous stimulation of excitable tissue, which may cause pain, discomfort or other sensation or perception of the stimulation. In other applications, the therapy delivery electrodes may be in direct contact with the targeted body tissue but the electrical current of the stimulation pulses may spread to neighboring tissues causing extraneous stimulation. The techniques disclosed herein provide for delivery of high frequency electrical stimulation pulses to reduce pain or sensation due to delivery of the electrical stimulation pulses. The high frequency electrical stimulation pulses are modulated to cause depolarization of a targeted tissue, e.g., cardiac, muscle or nerve, by the delivered electrical stimulation pulses for a therapeutic or medical purpose.

In the illustrative examples presented herein, a cardiac medical device, such as a pacemaker or ICD, is configured to deliver cardiac electrical stimulation pulses for capturing and depolarizing the myocardium. The pacemaker or ICD may be coupled to extracardiac or extracardiovascular electrodes in various examples. As used herein, the term "extra-cardiovascular" refers to a position outside the blood vessels, heart, and pericardium surrounding the heart of a patient. Implantable electrodes carried by extra-cardiovascular leads, for example, may be positioned extra-thoracically (outside the ribcage and sternum) or intra-thoracically (beneath the ribcage or sternum, sometimes referred to as a sub-sternal position) but may not necessarily be in intimate contact with myocardial tissue. In other examples, the medical device may be coupled to a transvenous lead that positions electrodes within a blood vessel but may remain outside the heart in an "extra-cardiac" location. For example, a transvenous medical lead may be advanced along a venous pathway to position electrodes within the internal thoracic vein (ITV), an intercostal vein, the superior epigastric vein, or the azygos, hemiazygos, or accessory hemiazygos veins, as examples. In any of these positions, e.g., extra-cardiovascular or extra-cardiac, an electrical field surrounding the electrodes produced by the electrical stimulation pulses being delivered to the heart may encompass skeletal muscle and nerves.

When cardiac pacing pulses or other cardiac electrical stimulation pulses are delivered having a pulse amplitude and pulse width required to capture the patient's heart but do not employ the modulation techniques disclosed herein, the patient may perceive the cardiac pacing and/or experience pain, discomfort or other sensation. Persistent cardiac pacing in a patient that requires frequent or sustained episodes of cardiac pacing may not be well tolerated. The techniques for generating and delivering modulated pacing pulses to reduce pain and perception of delivered cardiac pacing pulses may enable an extra-cardiac or extracardiovascular pacemaker or ICD system to deliver a wider variety of cardiac pacing therapies for treating a variety of arrhythmias including bradycardia, atrioventricular block, asystole, or ventricular tachycardia as examples.

The electrical stimulation techniques disclosed herein may be implemented in a variety of medical devices, however, including implantable pacemakers, ICDs, neurostimulators, muscle stimulators, brain stimulators, spinal cord stimulators, or other devices configured to deliver therapeutic electrical stimulation pulses. In some examples, the electrodes delivering the stimulation pulses are carried by a medical electrical lead extending away from the medical device. In other examples, the electrodes may be on the housing of the medical device. The techniques disclosed herein for delivering modulated electrical stimulation pulses are not limited to a particular medical device lead or electrode configuration.

Figure 1B:
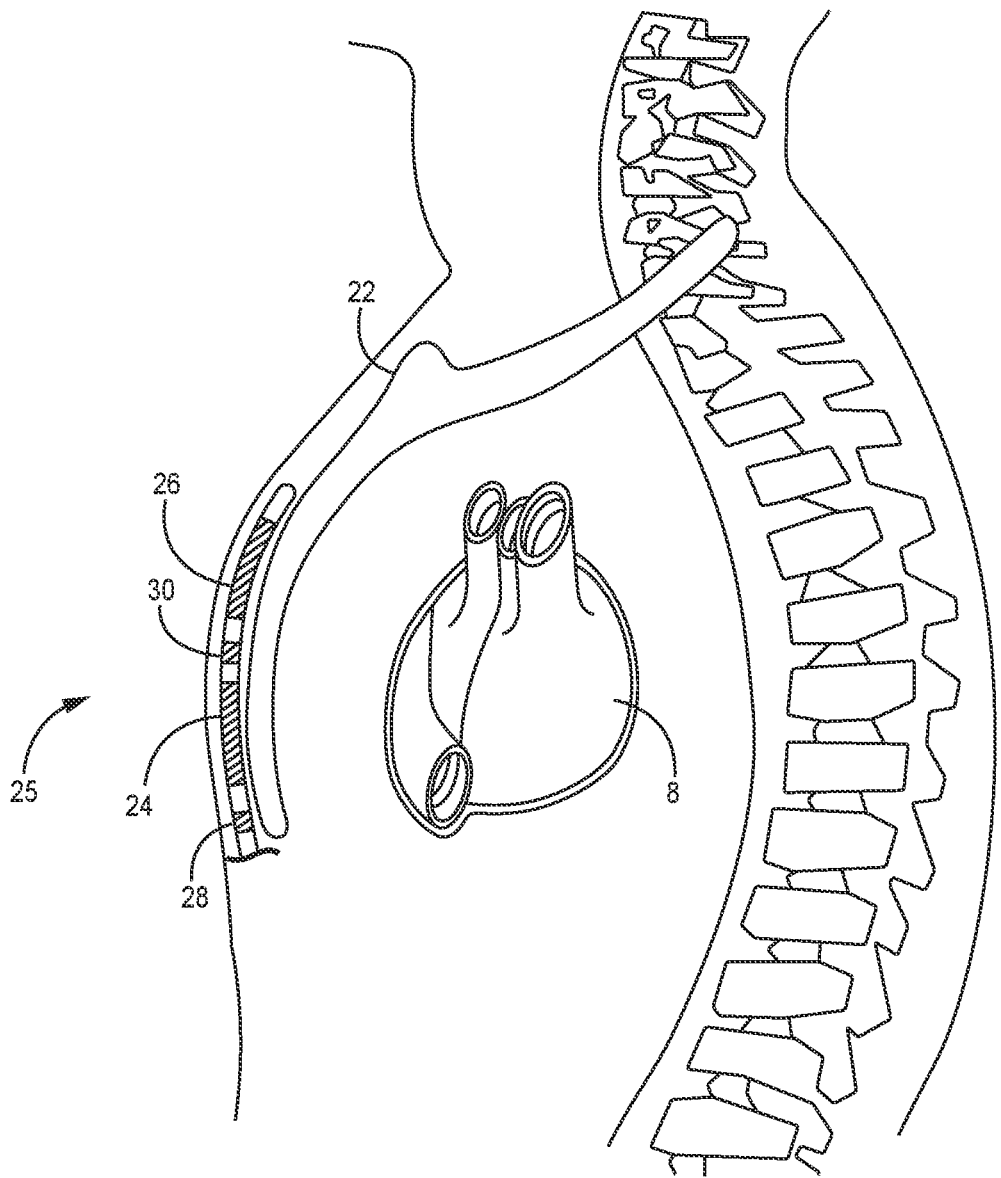

FIGS. 1A and 1B are conceptual diagrams of an example medical device system 10 that may employ the electrical stimulation pulse modulation techniques disclosed herein. System 10 includes an ICD 14, lead 16, and an external device 40. ICD 14 is configured to sense cardiac electrical signals and deliver cardiac electrical stimulation therapies via electrodes carried by lead 16. FIG. 1A is a front view of ICD 14 and lead 16 implanted within patient 12. FIG. 1B is a side view of ICD 14 and lead 16 implanted within patient 12. FIGS. 1A and 1B are described in the context of an ICD 14 capable of providing high voltage cardioversion/defibrillation (CV/DF) shocks and relatively lower voltage cardiac pacing pulses in response to detecting a cardiac arrhythmia. However, the techniques disclosed herein may be implemented in other cardiac devices configured for delivering only cardiac pacing therapies or only high voltage CV/DF shocks.

ICD 14 includes a housing 15 that forms a hermetic seal that protects internal components of ICD 14. The housing 15 of ICD 14 may be formed of a conductive material, such as titanium or titanium alloy. The housing 15 may function as an electrode (sometimes referred to as a "can" electrode). Housing 15 may be used as an active can electrode for use in delivering CV/DF shocks or other high voltage pulses delivered using a high voltage therapy circuit. In other examples, housing 15 may be available for use in delivering unipolar, lower voltage cardiac pacing pulses and/or for sensing cardiac electrical signals in combination with electrodes carried by lead 16. In other instances, the housing 15 of ICD 14 may include a plurality of electrodes on an outer portion of the housing. The outer portion(s) of the housing 15 functioning as an electrode(s) may be coated with a material, such as titanium nitride, e.g., for reducing post-stimulation polarization artifact.

ICD 14 includes a connector assembly 17 (also referred to as a connector block or header) that includes electrical feedthroughs crossing housing 15 to provide electrical connections between conductors extending within the lead body 18 of lead 16 and electronic components included within the housing 15 of ICD 14. As will be described in further detail herein, housing 15 may house one or more processors, memories, transceivers, cardiac electrical signal sensing circuitry, therapy delivery circuitry, power sources and other components for sensing cardiac electrical signals, detecting a heart rhythm, and controlling and delivering electrical stimulation pulses to treat an abnormal heart rhythm.

Elongated lead body 18 has a proximal end 27 that includes a lead connector (not shown) configured to be connected to ICD connector assembly 17 and a distal portion 25 that includes one or more electrodes. In the example illustrated in FIGS. 1A and 1B, the distal portion 25 of lead body 18 includes defibrillation electrodes 24 and 26 and pace/sense electrodes 28 and 30. In some cases, defibrillation electrodes 24 and 26 may together form a defibrillation electrode in that they may be configured to be activated concurrently. Alternatively, defibrillation electrodes 24 and 26 may form separate defibrillation electrodes in which case each of the electrodes 24 and 26 may be activated independently.

Electrodes 24 and 26 (and in some examples housing 15) are referred to herein as defibrillation electrodes because they are utilized, individually or collectively, for delivering high voltage stimulation therapy (e.g., CV/DF shocks). Electrodes 24 and 26 may be elongated coil electrodes and generally have a relatively high surface area for delivering high voltage electrical stimulation pulses compared to pacing and sensing electrodes 28 and 30. However, electrodes 24 and 26 and housing 15 may also be utilized to provide pacing functionality, sensing functionality or both pacing and sensing functionality in addition to or instead of high voltage stimulation therapy. In this sense, the use of the term "defibrillation electrode" herein should not be considered as limiting the electrodes 24 and 26 for use in only high voltage cardioversion/defibrillation shock therapy applications. For example, either of electrodes 24 and 26 may be used as a sensing electrode in a sensing vector for sensing cardiac electrical signals and determining a need for an electrical stimulation therapy.

Electrodes 28 and 30 are relatively smaller surface area electrodes which are available for use in sensing electrode vectors for sensing cardiac electrical signals and may be used for delivering relatively low voltage pacing pulses in some configurations. Electrodes 28 and 30 are referred to as pace/sense electrodes because they are generally configured for use in low voltage applications, e.g., used as either a cathode or anode for delivery of pacing pulses and/or sensing of cardiac electrical signals, as opposed to delivering high voltage CV/DF shocks. In some instances, electrodes 28 and 30 may provide only pacing functionality, only sensing functionality or both. The cardiac electrical stimulation pulses disclosed herein may be delivered by any combination of the available electrodes 24, 26, 28, 30 and/or housing 15. ICD 14 may sense cardiac electrical signals corresponding to electrical activity of heart 8 via a combination of sensing electrode vectors that include combinations of electrodes 24, 26, 28 and/or 30. In some examples, housing 15 of ICD 14 is used in combination with one or more of electrodes 24, 26, 28 and/or 30 in a sensing electrode vector.

In the example illustrated in FIGS. 1A and 1B, electrode 28 is located proximal to defibrillation electrode 24, and electrode 30 is located between defibrillation electrodes 24 and 26. One, two or more pace/sense electrodes may be carried by lead body 18. For instance, a third pace/sense electrode may be located distal to defibrillation electrode 26 in some examples. Electrodes 28 and 30 are illustrated as ring electrodes; however, electrodes 28 and 30 may comprise any of a number of different types of electrodes, including ring electrodes, short coil electrodes, hemispherical electrodes, directional electrodes, segmented electrodes, or the like. Electrodes 28 and 30 may be positioned at other locations along lead body 18 and are not limited to the positions shown. In other examples, lead 16 may include fewer or more pace/sense electrodes and/or defibrillation electrodes than the example shown here.

In the example shown, lead 16 extends subcutaneously or submuscularly over the ribcage 32 medially from the connector assembly 27 of ICD 14 toward a center of the torso of patient 12, e.g., toward xiphoid process 20 of patient 12. At a location near xiphoid process 20, lead 16 bends or turns and extends superiorly, subcutaneously or submuscularly, over the ribcage and/or sternum, substantially parallel to sternum 22. Although illustrated in FIG. 1A as being offset laterally from and extending substantially parallel to sternum 22, the distal portion 25 of lead 16 may be implanted at other locations, such as over sternum 22, offset to the right or left of sternum 22, angled laterally from sternum 22 toward the left or the right, or the like. Alternatively, lead 16 may be placed along other subcutaneous or submuscular paths. The path of extra-cardiovascular lead 16 may depend on the location of ICD 14, the arrangement and position of electrodes carried by the lead body 18, and/or other factors.

Electrical conductors (not illustrated) extend through one or more lumens of the elongated lead body 18 of lead 16 from the lead connector at the proximal lead end 27 to electrodes 24, 26, 28, and 30 located along the distal portion 25 of the lead body 18. The elongated electrical conductors contained within the lead body 18, which may be separate respective insulated conductors within the lead body 18, are each electrically coupled with respective defibrillation electrodes 24 and 26 and pace/sense electrodes 28 and 30. The respective conductors electrically couple the electrodes 24, 26, 28, and 30 to circuitry, such as a therapy delivery circuit and/or a sensing circuit, of ICD 14 via connections in the connector assembly 17, including associated electrical feedthroughs crossing housing 15. The electrical conductors transmit therapy from a therapy delivery circuit within ICD 14 to one or more of defibrillation electrodes 24 and 26 and/or pace/sense electrodes 28 and 30 and transmit sensed electrical signals produced by the patient's heart 8 from one or more of defibrillation electrodes 24 and 26 and/or pace/sense electrodes 28 and 30 to the sensing circuit within ICD 14.

The lead body 18 of lead 16 may be formed from a non-conductive material, including silicone, polyurethane, fluoropolymers, mixtures thereof, and/or other appropriate materials, and shaped to form one or more lumens within which the one or more conductors extend. Lead body 18 may be tubular or cylindrical in shape. In other examples, the distal portion 25 (or all of) the elongated lead body 18 may have a flat, ribbon or paddle shape. Lead body 18 may be formed having a preformed distal portion 25 that is generally straight, curving, bending, serpentine, undulating or zig-zagging.

In the example shown, lead body 18 includes a curving distal portion 25 having two "C" shaped curves, which together may resemble the Greek letter epsilon, "ε." Defibrillation electrodes 24 and 26 are each carried by one of the two respective C-shaped portions of the lead body distal portion 25. The two C-shaped curves are seen to extend or curve in the same direction away from a central axis of lead body 18, along which pace/sense electrodes 28 and 30 are positioned. Pace/sense electrodes 28 and 30 may, in some instances, be approximately aligned with the central axis of the straight, proximal portion of lead body 18 such that mid-points of defibrillation electrodes 24 and 26 are laterally offset from pace/sense electrodes 28 and 30.

Other examples of extra-cardiovascular leads including one or more defibrillation electrodes and one or more pacing and sensing electrodes carried by curving, serpentine, undulating or zig-zagging distal portion of the lead body 18 that may be implemented with the techniques described herein are generally disclosed in pending U.S. Pat. Publication No. 2016/0158567 (Marshall, et al.), incorporated herein by reference in its entirety. The techniques disclosed herein are not limited to any particular lead body design or electrode arrangement, however. In other examples, lead body 18 is a flexible elongated lead body without any pre-formed shape, bends or curves.

ICD 14 analyzes the cardiac electrical signals received from one or more sensing electrode vectors to monitor for abnormal rhythms, such as asystole, bradycardia, ventricular tachycardia (VT) or ventricular fibrillation (VF). ICD 14 may analyze the heart rate and morphology of the cardiac electrical signals to monitor for tachyarrhythmia in accordance with any of a number of tachyarrhythmia detection techniques.

ICD 14 generates and delivers electrical stimulation therapy in response to detecting a tachyarrhythmia (e.g., VT or VF) using a therapy delivery electrode vector which may be selected from any of the available electrodes 24, 26, 28, 30 and/or housing 15. ICD 14 may deliver anti-tachycardia pacing (ATP) in response to VT detection and in some cases may deliver ATP prior to a CV/DF shock or during high voltage capacitor charging in an attempt to avert the need for delivering a CV/DF shock. If ATP does not successfully terminate VT or when VF is detected, ICD 14 may deliver one or more CV/DF shocks via one or both of defibrillation electrodes 24 and 26 and/or housing 15. ICD 14 may deliver the CV/DF shocks using electrodes 24 and 26 individually or together as a cathode (or anode) and with the housing 15 as an anode (or cathode). ICD 14 may generate and deliver other types of electrical stimulation pulses such as post-shock pacing pulses or bradycardia pacing pulses using a pacing electrode vector that includes one or more of the electrodes 24, 26, 28, and 30 and the housing 15 of ICD 14.

ICD 14 is shown implanted subcutaneously on the left side of patient 12 along the ribcage 32. ICD 14 may, in some instances, be implanted between the left posterior axillary line and the left anterior axillary line of patient 12. ICD 14 may, however, be implanted at other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferiorly from the manubrium to the desired location subcutaneously or submuscularly. In yet another example, ICD 14 may be placed abdominally. Lead 16 may be implanted in other extra-cardiac or extra-cardiovascular locations as well. For instance, as described with respect to FIGS. 2A-2C, the distal portion 25 of lead 16 may be implanted underneath the sternum/ribcage in the substernal space. FIGS. 1A and 1B are illustrative in nature and should not be considered limiting of the practice of the techniques disclosed herein.

An external device 40 is shown in telemetric communication with ICD 14 by a communication link 42. External device 40 may include a processor 52, memory 53, display 54, user interface 56 and telemetry unit 58. Processor 52 controls external device operations and processes data and signals received from ICD 14. Display 54, which may include a graphical user interface, displays data and other information to a user for reviewing ICD operation and programmed parameters as well as cardiac electrical signals retrieved from ICD 14.

User interface 56 may include a mouse, touch screen, key pad or the like to enable a user to interact with external device 40 to initiate a telemetry session with ICD 14 for retrieving data from and/or transmitting data to ICD 14, including programmable parameters for controlling cardiac event sensing and therapy delivery. Telemetry unit 58 includes a transceiver and antenna configured for bidirectional communication with a telemetry circuit included in ICD 14 and is configured to operate in conjunction with processor 52 for sending and receiving data relating to ICD functions via communication link 42.

Communication link 42 may be established between ICD 14 and external device 40 using a radio frequency (RF) link such as BLUETOOTH®, Wi-Fi, or Medical Implant Communication Service (MICS) or other RF or communication frequency bandwidth or communication protocols. Data stored or acquired by ICD 14, including physiological signals or associated data derived therefrom, results of device diagnostics, and histories of detected rhythm episodes and delivered therapies, may be retrieved from ICD 14 by external device 40 following an interrogation command.

External device 40 may be embodied as a programmer used in a hospital, clinic or physician's office to retrieve data from ICD 14 and to program operating parameters and algorithms in ICD 14 for controlling ICD functions. External device 40 may alternatively be embodied as a home monitor or hand held device. External device 40 may be used to program cardiac signal sensing parameters, cardiac rhythm detection parameters and therapy control parameters used by ICD 14. At least some control parameters used in generating and delivering modulated cardiac electrical stimulation pulses according to techniques disclosed herein may be programmed into ICD 14 using external device 40 in some examples. In some examples, the patient 12 or a caregiver may use external device 40 to transmit a pain notification signal to ICD 14 when the patient perceives delivered electrical stimulation pulses or experiences pain associated therewith. As described below in conjunction with FIG. 11, ICD 14 may be configured to adjust modulation of cardiac electrical stimulation pulse signals to reduce the pain or perception of delivered electrical stimulation pulses.

Figure 2A:
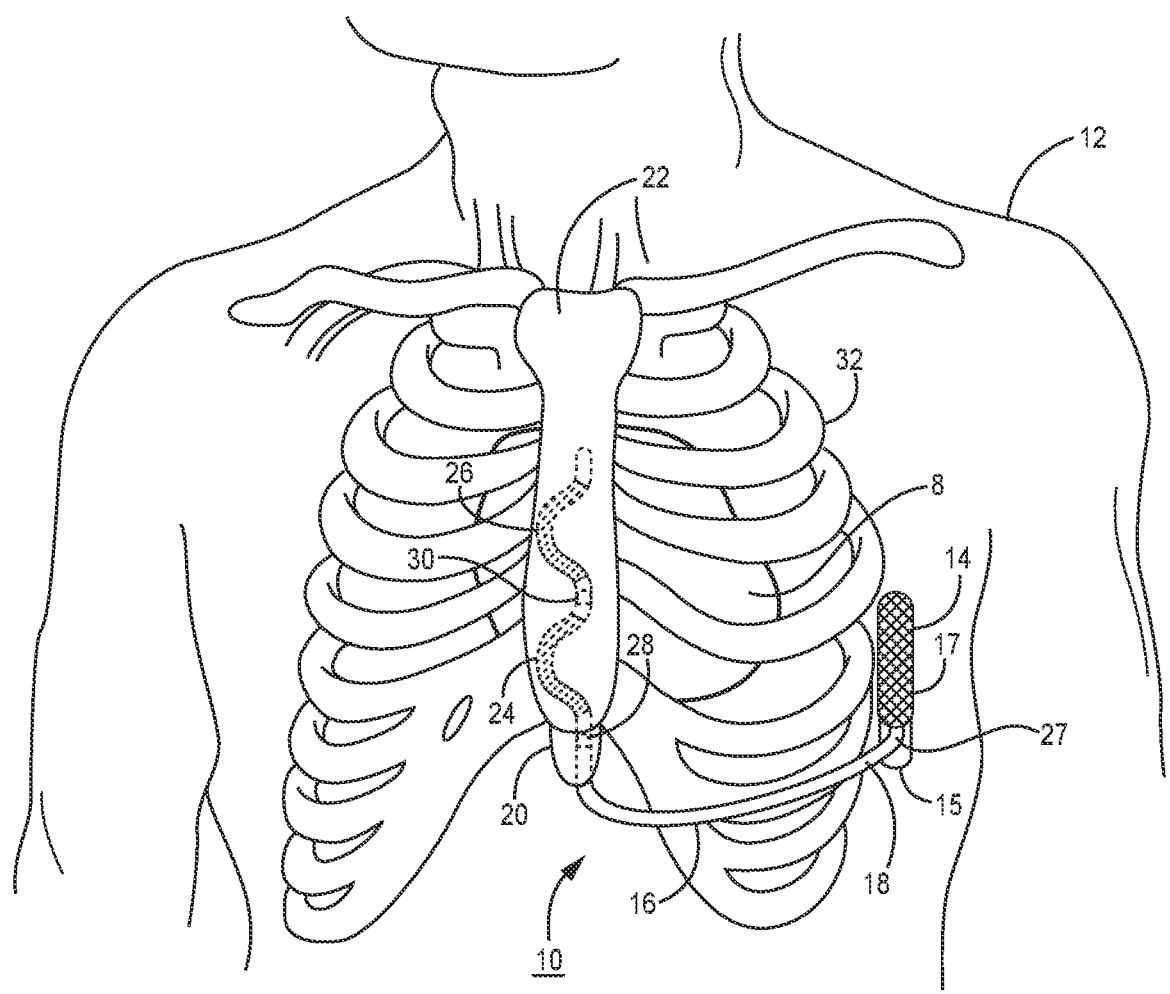
FIGS. 2A-2C are conceptual diagrams of a patient implanted with an extra-cardiovascular ICD system in a different implant configuration than the arrangement shown in FIGS. 1A-1B.
Figure 2B:
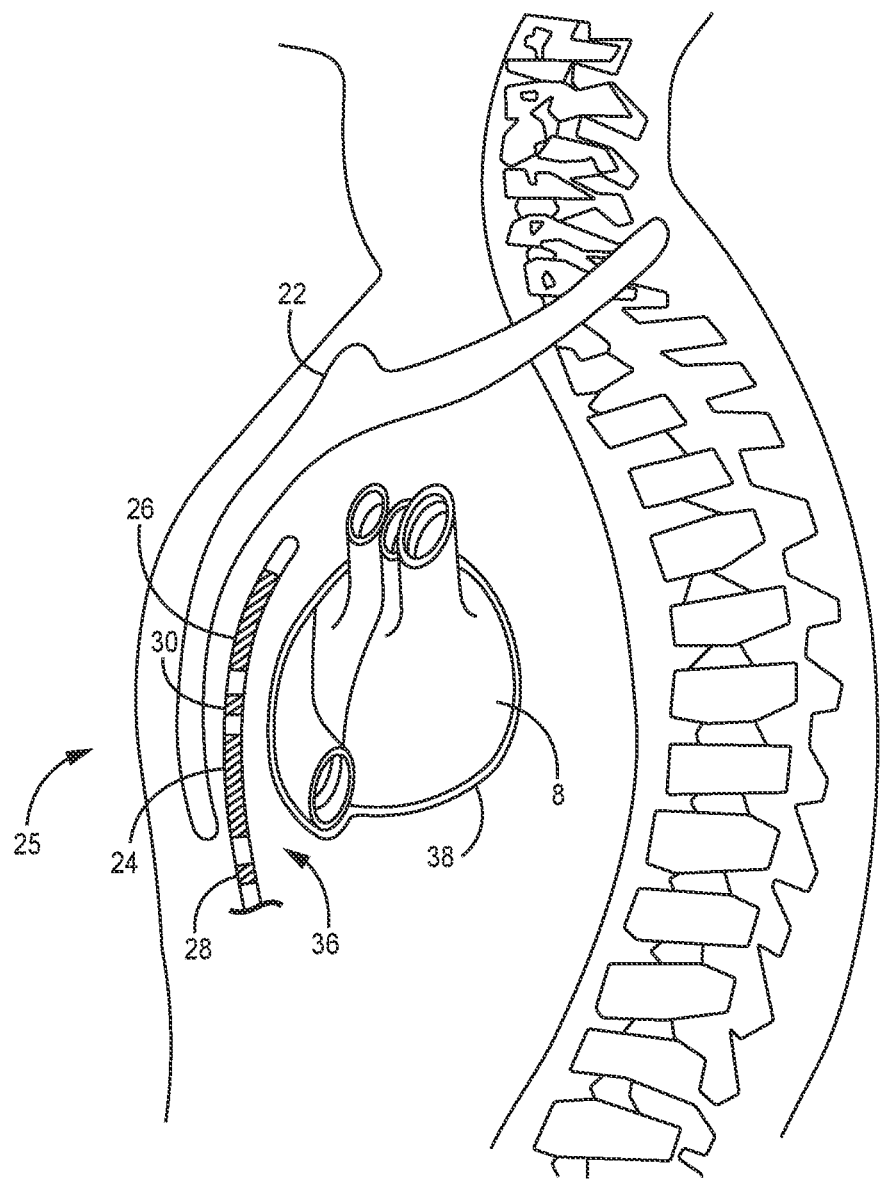
Figure 2C:
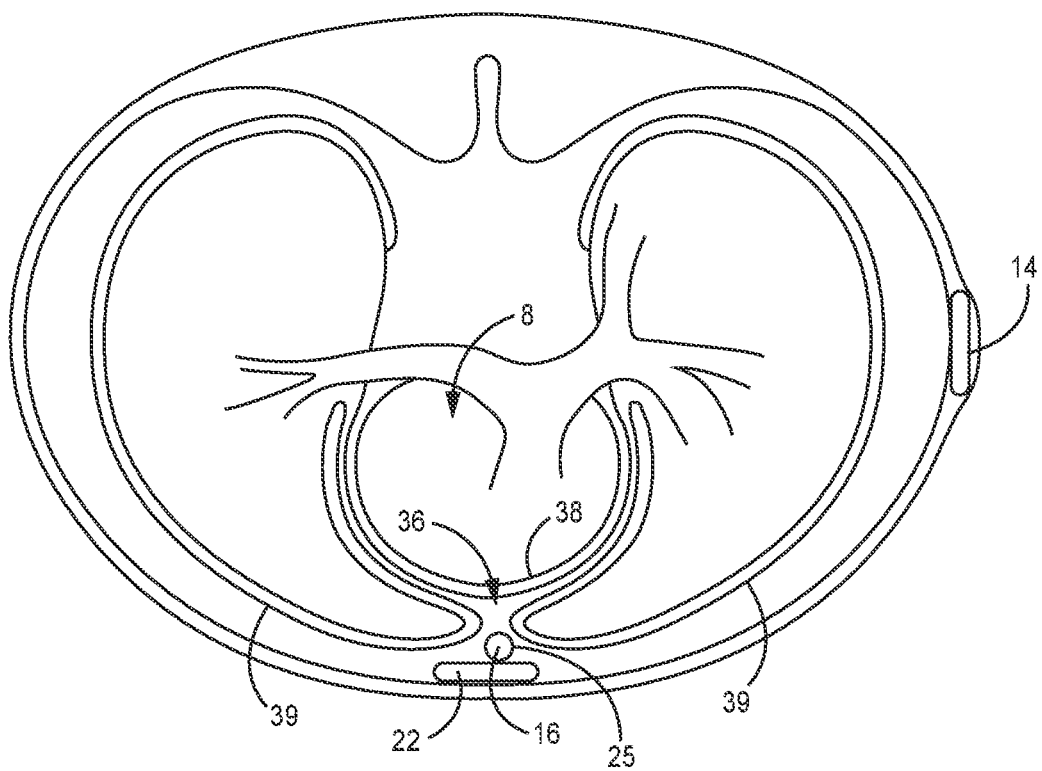

FIGS. 2A-2C are conceptual diagrams of patient 12 implanted with lead 16 in a different implant configuration than the arrangement shown in FIGS. 1A-1B. FIG. 2A is a front view of patient 12 implanted with system 10. FIG. 2B is a side view of patient 12 implanted with system 10. FIG. 2C is a transverse view of patient 12 implanted with system 10. In this arrangement lead 16 of system 10 is implanted in an extra-cardiovascular location at least partially underneath sternum 22 of patient 12. Lead 16 extends subcutaneously or submuscularly from ICD 14 toward xiphoid process 20 and at a location near xiphoid process 20 bends or turns and extends superiorly within anterior mediastinum 36 in a substernal position.

Anterior mediastinum 36 may be viewed as being bounded laterally by pleurae 39, posteriorly by pericardium 38, and anteriorly by sternum 22 (see FIG. 2C). The distal portion 25 of lead 16 may extend along the posterior side of sternum 22 substantially within the loose connective tissue and/or substernal musculature of anterior mediastinum 36. A lead implanted such that the distal portion 25 is substantially within anterior mediastinum 36, may be referred to as a "substernal lead."

In the example illustrated in FIGS. 2A-2C, lead 16 is located substantially centered under sternum 22. In other instances, however, lead 16 may be implanted such that it is offset laterally from the center of sternum 22. In some instances, lead 16 may extend laterally such that distal portion 25 of lead 16 is underneath/below the ribcage 32 in addition to or instead of sternum 22. In other examples, the distal portion 25 of lead 16 may be implanted in other extra-cardiovascular, intra-thoracic locations, including the pleural cavity or around the perimeter of and adjacent to the pericardium 38 of heart 8. For example, the distal portion 25 of lead 16 may be advanced to a supra-diaphragmatic position, which may be within the thoracic cavity or outside the thorax in various examples. As described above, lead 16 may alternatively be advanced within a vein to position electrodes for delivering electrical stimulation pulses to heart 8 from an intravenous location.

Figure 3:
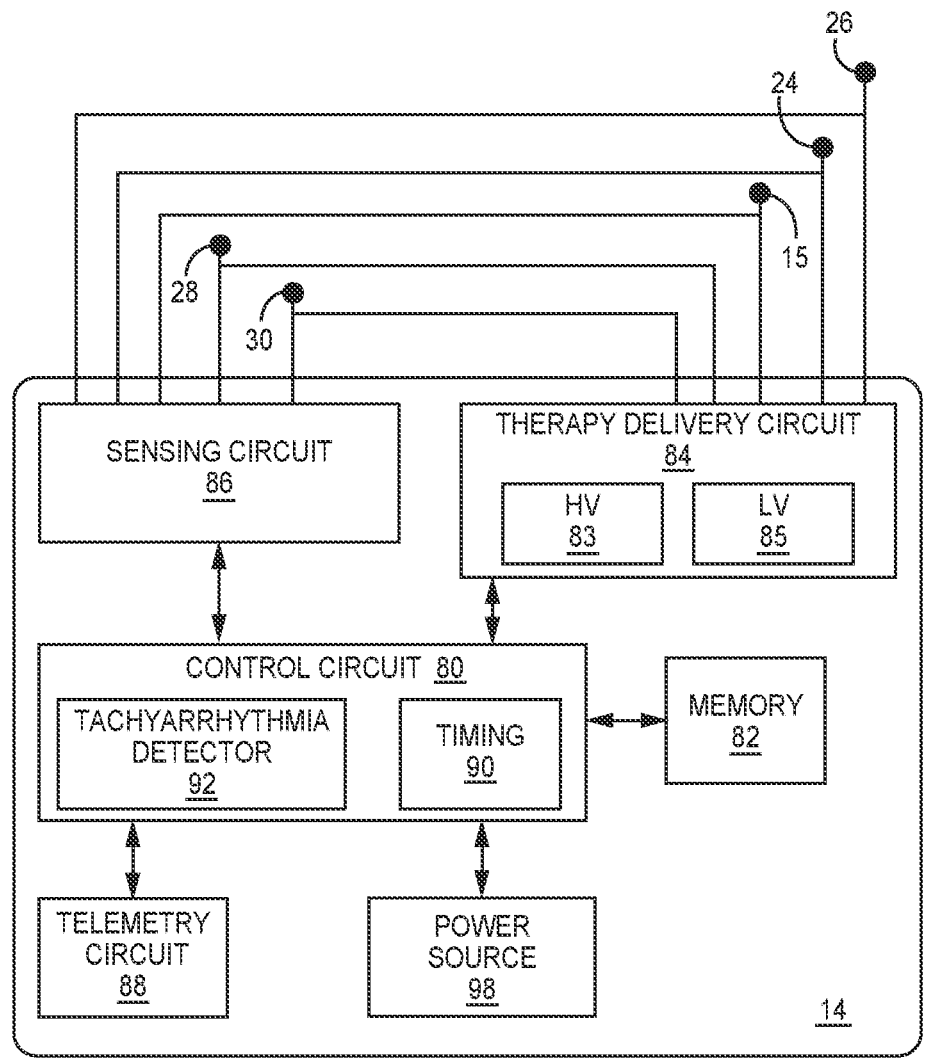
FIG. 3 is a conceptual diagram of a medical device configured to generate modulated electrical stimulation pulse signals according to one example.

FIG. 3 is a conceptual diagram of circuitry which may be included in a medical device, e.g., ICD 14, configured to deliver modulated electrical stimulation pulses according to one example. The electronic circuitry enclosed within housing 15 (shown schematically as an electrode in FIG. 3) includes software, firmware and hardware that cooperatively monitor cardiac electrical signals, determine when an electrical stimulation therapy is necessary, and deliver therapy as needed according to programmed therapy delivery algorithms and control parameters. ICD 14 may be coupled to a lead, such as lead 16 carrying electrodes 24, 26, 28, and 30, that may be positioned in an extra-cardiac or extracardiovascular location for delivering electrical stimulation pulses to the patient's heart and for sensing cardiac electrical signals. In various examples, ICD 14 may be coupled to an extra-cardiac transvenous lead, subcutaneous, submuscular, or substernal lead carrying electrodes, e.g., electrodes 24, 26, 28 and 30 for sensing cardiac electrical signals and delivering electrical stimulation pulses to the patient's heart.

ICD 14 includes a control circuit 80, memory 82, therapy delivery circuit 84, cardiac electrical signal sensing circuit 86, and telemetry circuit 88. A power source 98 provides power to the circuitry of ICD 14, including each of the components 80, 82, 84, 86, and 88, as needed. Power source 98 may include one or more energy storage devices, such as one or more rechargeable or non-rechargeable batteries. The connections between power source 98 and each of the other components 80, 82, 84, 86 and 88 are to be understood from the general block diagram of FIG. 3, but are not shown for the sake of clarity. For example, power source 98 may be coupled to one or more charging circuits included in therapy delivery circuit 84 for charging holding capacitors included in therapy delivery circuit 84 that are discharged at appropriate times under the control of control circuit 80 for producing electrical pulses according to a therapy protocol. Power source 98 is also coupled to components of cardiac electrical signal sensing circuit 86, such as sense amplifiers, analog-to-digital converters, switching circuitry, etc. as needed to perform the cardiac electrical signal sensing functionality of sensing circuit 86 as described herein.

The circuits shown in FIG. 3 represent functionality included in ICD 14 and may include any discrete and/or integrated electronic circuit components that implement analog and/or digital circuits capable of producing the functions attributed to ICD 14 herein. Functionality associated with one or more circuits may be performed by separate hardware, firmware or software components, or integrated within common hardware, firmware or software components. For example, cardiac electrical signal sensing (e.g., R-waves and/or P-wave sensing) and detection of tachyarrhythmia, bradycardia or asystole may be performed cooperatively by sensing circuit 86 and control circuit 80 and may include operations implemented in a processor or other signal processing circuitry included in control circuit 80 executing instructions stored in memory 82 and control signals such as blanking and timing intervals and sensing threshold amplitude signals sent from control circuit 80 to sensing circuit 86.

The various circuits of ICD 14 may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. The particular form of software, hardware and/or firmware employed to implement the functionality disclosed herein will be determined primarily by the particular system architecture employed in the ICD and by the particular detection and therapy delivery methodologies employed by the ICD. Providing software, hardware, and/or firmware to accomplish the described functionality in the context of any modern medical device, given the disclosure herein, is within the abilities of one of skill in the art.

Memory 82 may include any volatile, non-volatile, magnetic, or electrical non-transitory computer readable storage media, such as random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control circuit 80 and/or other ICD components to perform various functions attributed to ICD 14 or those ICD components. The non-transitory computer-readable media storing the instructions may include any of the media listed above.

Control circuit 80 communicates, e.g., via a data bus, with therapy delivery circuit 84 and sensing circuit 86 for sensing cardiac electrical activity, detecting cardiac rhythms, and controlling delivery of cardiac electrical stimulation therapies in response to sensed cardiac signals. Therapy delivery circuit 84 and sensing circuit 86 are electrically coupled to electrodes 24, 26, 28, 30 carried by lead 16 and the housing 15, which may function as a common or ground electrode or as an active can electrode for delivering CV/DF shock pulses or cardiac pacing pulses.

Sensing circuit 86 may be selectively coupled to electrodes 28, 30 and/or housing 15 in order to monitor electrical activity of the patient's heart. Sensing circuit 86 may additionally be selectively coupled to defibrillation electrodes 24 and/or 26 for use in a sensing electrode vector together or in combination with one or more of electrodes 28, 30 and/or housing 15. Sensing circuit 86 may be enabled to selectively receive cardiac electrical signals from one or more sensing electrode vectors from the available electrodes 24, 26, 28, 30, and housing 15. At least two cardiac electrical signals from two different sensing electrode vectors may be received simultaneously by sensing circuit 86 in some examples. Sensing circuit 86 may monitor one or both of the cardiac electrical signals simultaneously for sensing cardiac electrical events and/or producing digitized cardiac signal waveforms for analysis by control circuit 80. For example, sensing circuit 86 may include two sensing channels and switching circuitry for selecting which of electrodes 24, 26, 28, 30, and housing 15 are coupled to a first sensing channel and which electrodes are coupled to a second sensing channel of sensing circuit 86.

Each sensing channel may be configured to amplify, filter and digitize the cardiac electrical signal received from selected electrodes coupled to the respective sensing channel to improve the signal quality for detecting cardiac electrical events, such as R-waves attendant to ventricular depolarization (pacing evoked or intrinsic) and/or P-waves attendant to atrial depolarizations, or performing other signal analysis. The cardiac event detection circuitry within sensing circuit 86 may include one or more sense amplifiers, filters, rectifiers, threshold detectors, comparators, analog-to-digital converters (ADCs), timers or other analog or digital components. A cardiac event sensing threshold may be automatically adjusted by sensing circuit 86 under the control of control circuit 80, based on timing intervals and sensing threshold values determined by control circuit 80, stored in memory 82, and/or controlled by hardware, firmware and/or software of control circuit 80 and/or sensing circuit 86.

Upon detecting a cardiac event based on a sensing threshold crossing, sensing circuit 86 may produce a sensed event signal, such as an R-wave sensed event signal, that is passed to control circuit 80. Timing circuit 90 included in control circuit 80 may set a pacing escape interval in response to an R-wave sensed event signal and/or a delivered pacing pulse. The pacing escape interval may be a programmed lower rate interval, a back-up pacing rate interval, a post-shock pacing interval or other asystole, bradycardia or tachycardia therapy pacing interval used to control the timing of a pacing pulse delivered according to therapy control parameters and using the modulation techniques disclosed herein. Control circuit 80 may be configured to operate in a variety of pacing modes including demand or triggered bradycardia pacing modes, including rate responsive pacing modes.

R-wave sensed event signals may also be used by control circuit 80 for determining R-to-R intervals (RRIs) for detecting arrhythmia and determining a need for therapy. An RRI is the time interval between consecutively sensed R-waves and may be determined between consecutive R-wave sensed event signals received from sensing circuit 86. For example, control circuit 80 may include a timing circuit 90 for determining RRIs between consecutive R-wave sensed event signals received from sensing circuit 86 and for controlling various timers and/or counters used to control the timing of therapy delivery by therapy delivery circuit 84. Timing circuit 90 may additionally set time windows such as morphology template windows, morphology analysis windows or perform other timing related functions of ICD 14 including synchronizing CV/DF shocks or other therapies delivered by therapy delivery circuit 84 with sensed cardiac events.

Control circuit 80 is also shown to include a tachyarrhythmia detector 92 configured to analyze signals received from sensing circuit 86 for detecting tachyarrhythmia episodes. Tachyarrhythmia detector 92 may be implemented in control circuit 80 as hardware, software and/or firmware that processes and analyzes signals received from sensing circuit 86 for detecting VT and/or VF. The timing of R-wave sense event signals received from sensing circuit 86 is used by timing circuit 90 to determine RRIs between consecutive sensed event signals. Tachyarrhythmia detector 92 may include comparators and counters for counting RRIs determined by timing circuit 92 that fall into various rate detection zones for determining a ventricular rate or performing other rate- or interval-based assessments for detecting and discriminating VT and VF.

For example, tachyarrhythmia detector 92 may compare the RRIs determined by timing circuit 90 to one or more tachyarrhythmia detection interval zones, such as a tachycardia detection interval zone and a fibrillation detection interval zone. RRIs falling into a detection interval zone are counted by a respective VT interval counter or VF interval counter, and in some cases in a combined VT/VF interval counter, included in tachyarrhythmia detector 92. When an interval counter value reaches a detection threshold number of intervals, a ventricular tachyarrhythmia may be detected by tachyarrhythmia detector 92. Tachyarrhythmia detector 92 may be configured to perform other signal analysis for determining if other detection criteria are satisfied before detecting VT or VF, such as R-wave morphology criteria, onset criteria, and noise and oversensing rejection criteria.

To support these additional analyses, sensing circuit 86 may pass a digitized cardiac electrical signal, e.g., an electrocardiogram (ECG) signal, to control circuit 80 for morphology analysis performed by tachyarrhythmia detector 92. A cardiac electrical signal may be passed through a filter and amplifier, provided to a multiplexer and thereafter converted to multi-bit digital signals by an analog-to-digital converter, all included in sensing circuit 86, for storage in memory 82. Memory 82 may include one or more circulating buffers to temporarily store digital cardiac electrical signal segments for analysis performed by control circuit 80. Control circuit 80 may be a microprocessor-based controller that employs digital signal analysis techniques to characterize the digitized signals stored in memory 82 to recognize and classify individual beats and the patient's heart rhythm employing any of numerous signal processing methodologies for analyzing cardiac signals and cardiac event waveforms, e.g., R-waves.

Therapy delivery circuit 84 includes a signal source, modulator and output circuit as described below in conjunction with FIG. 6. The signal source may include charging circuitry coupled to the power source 98, one or more charge storage devices such as one or more high voltage capacitors and/or low voltage capacitors, and switching circuitry that controls when the capacitor(s) are charged and discharged across a selected pacing electrode vector or CV/DF shock vector. Charging of capacitors to a programmed pulse amplitude and discharging of the capacitors for a programmed pulse width via a modulator and output circuit may be performed by therapy delivery circuit 84 according to control signals received from control circuit 80 as described below. In other examples, the signal source may be a voltage regulator or current regulator coupled to power source 98 and configured to pass a voltage or current controlled signal to the modulator for generating a modulated, high frequency electrical stimulation pulse signal.

Control circuit 80 may include various timers or counters that control when cardiac pacing pulses are delivered. For example, timing circuit 90 may include programmable digital counters set by a microprocessor of the control circuit 80 for controlling the basic pacing time intervals associated with various pacing modes or ATP sequences delivered by ICD 14. The microprocessor of control circuit 80 may also set the pulse amplitude, pulse width, maximum frequency, minimum frequency, maximum bias offset, minimum bias offset, rates of modulation of the frequency, amplitude and bias, or other control parameters used in generating cardiac electrical stimulation pulses, which may be based on programmed values stored in memory 82. As disclosed herein, control circuit 80 may set control signals passed to therapy delivery circuit 84 for controlling amplitude modulation, frequency modulation and/or bias modulation of the cardiac electrical stimulation pulses. For example, control circuit 80 may set control signals passed to therapy delivery circuit 84 for controlling maximum and minimum frequencies in a frequency modulated pacing pulse and the time intervals over which the frequency is increased and decreased. In other examples, control circuit 80 may set control signals passed to therapy delivery circuit 84 for controlling a maximum and minimum offset of the bias of a cardiac electrical stimulation pulse signal and the rate of increasing and/or decreasing between the maximum and minimum offsets. These and other modulation control parameters are described below in conjunction with the accompanying diagrams and flow charts.

In some examples, therapy delivery circuit 84 may include a high voltage (HV) therapy circuit 83 and a low voltage (LV) therapy circuit 85. Therapy delivery circuit 84 may be configured to deliver high voltage therapies, e.g., relatively high voltage pacing pulses delivered by extracardiac electrodes and/or CV/DF shocks. Additionally or alternatively, therapy delivery circuit 84 may be configured to delivery relatively low voltage therapies, e.g., cardiac pacing pulses. Low voltage therapy circuit 85 may be configured to deliver relatively low voltage therapy by generating pulses having a maximum voltage and pulse energy much less than shock pulses delivered by HV therapy circuit 83, e.g., as described below. In other examples, therapy delivery circuit 84 is a single therapy circuit configured to generate therapeutic pulse signals over a range of voltage amplitudes and pulse energies as needed for a particular medical application.

Therapy delivery circuit 84 may include LV therapy circuit 85 for delivering low voltage pacing pulses using a pacing electrode vector selected from electrodes 24, 26, 28, 30 and/or housing 15. LV therapy circuit 85 may be configured to deliver low voltage pacing pulses, e.g., 8 V or less or 10 V or less in maximum pulse amplitude. One or more capacitors or other charge storage devices included in the LV therapy circuit 85 may be charged to a voltage according to a programmed pacing pulse amplitude by a LV charging circuit, which may include a state machine. The LV charging circuit may charge the capacitors to a multiple of the voltage of a battery included in power source 98 without requiring a transformer. At an appropriate time, the LV therapy circuit 85 couples the capacitor(s) to a pacing electrode vector to deliver a pacing pulse to the heart 8.

As described below, LV therapy circuit 85 may include a high frequency modulator for modulating the frequency of oscillations of the pacing pulse signals between a maximum frequency and a minimum frequency during the pacing pulse width. LV therapy circuit 85 may additionally include an amplitude modulator to modulate the amplitude of the pacing pulse during the pacing pulse width. LV therapy circuit 85 may additionally or alternatively include a low frequency bias generator for modulating the bias of the high frequency pacing pulse signal. LV therapy circuit 85 may generate a high frequency pacing pulse that is modulated according to modulation control parameters in response to receiving a pace timing signal from control circuit 80 according to any of the examples described herein.

High voltage (HV) therapy circuit 83 may include one or more high voltage capacitors. When a shockable rhythm is detected, the HV capacitors may be charged to a shock voltage amplitude by a HV charging circuit according to the programmed shock energy. The HV charging circuit may include a transformer and be a processor-controlled charging circuit that is controlled by control circuit 80. Control circuit 80 applies a signal to trigger discharge of the HV capacitor(s) upon detecting a feedback signal from therapy delivery circuit 84 that the HV capacitors have reached the shock voltage amplitude required to deliver the programmed shock energy. In this way, control circuit 80 controls operation of the high voltage therapy circuit 83 to deliver CV/DF shocks using defibrillation electrodes 24, 26 and/or housing 15.

HV therapy circuit 83 may be used to deliver cardiac pacing pulses in some examples. In this case, the HV capacitors may be charged to a much lower voltage than that used for delivering shock therapies, but the voltage may be higher than the maximum available pulse voltage amplitude produced by the LV therapy circuit 85. For example, the HV capacitor(s) may be charged to 40 V or less, 30 V or less or 20 V or less for producing pacing pulses. Compared to pacing pulses delivered by LV therapy circuit 85, pulses delivered by HV therapy circuit 83 may have a higher voltage amplitude and relatively longer pulse width for delivering higher energy pacing pulses for capturing the heart. More current may be delivered using a low impedance pacing electrode vector, e.g., between electrodes 24 and 26. A longer pulse width is attainable due to a higher capacitance (and consequently higher RC time constant) of the HV capacitor(s). The LV therapy circuit 85 may be capable of producing a maximum pulse voltage amplitude of up to and including 10 V in some examples. The maximum pacing pulse width produced by LV therapy circuit 85 may be 2 milliseconds (ms) due to the RC time constant associated with the low voltage capacitors of LV therapy circuit 85. Accordingly, in some patients, the HV therapy circuit 83 may respond to a pace timing signal from control circuit 80 for generating and delivering a cardiac pacing pulse according to the techniques disclosed heroin.

The HV therapy circuit 83 may be capable of producing a pulse voltage amplitude of 10 V or more having a relatively longer pacing pulse width, e.g., 10 ms or more, because of the higher capacitance (and high RC time constant) of high voltage capacitors included in HV therapy circuit 83. A typical HV pacing pulse width may be 10 ms; however example ranges of available pulse widths may be 0.2 ms to 20 ms or 20 ms up to 60 ms. An example of a maximum voltage amplitude that may be used for delivering high voltage pacing pulses may be 40 V. When a relatively higher pacing pulse voltage amplitude is tolerable by the patient, e.g., more than 10 V, a relatively shorter pacing pulse width, e.g., 2 to 5 ms, may be delivered by HV therapy circuit 83. However, a longer pacing pulse width may be used as needed, e.g., a 10 V, 20 ms pacing pulse.

For the sake of comparison, HV capacitor(s) that may be included in the HV therapy circuit 83 may be charged to an effective voltage greater than 100 V for delivering a cardioversion/defibrillation shock. For example, two or three HV capacitors may be provided in series having an effective capacitance of 148 to 155 microfarads in HV therapy circuit 83. These series capacitors may be charged to develop 100 to 800 V for the series combination in order to deliver shocks having a pulse energy of 5 Joules or more, and more typically 20 Joules or more.

In contrast, pacing pulses delivered by the HV therapy circuit 83 may have a pulse energy less than 1 Joule and even in the milliJoule range or tenths of milliJoules range depending on the pacing electrode impedance. For instance, a pacing pulse generated by HV therapy circuit 83 having a 10 V amplitude and 20 ms pulse width delivered using a pacing electrode vector between defibrillation electrodes 24 and 26, having an impedance in the range of 20 to 200 ohms, may have a delivered energy of 5 to 7 milliJoules. When a relatively shorter pulse width is used, e.g., down to 2 ms, the pacing pulse delivered by HV therapy circuit 83 using defibrillation electrodes 24 and 26 may be as low as 1 milliJoule. Cardiac pacing pulses delivered by HV therapy circuit 83 are expected to have a pacing voltage amplitude that is less than 100 V, and typically not more than 40 V, and deliver at least 1 milliJoule but less than 1 Joule of energy. The delivered energy for a given pacing voltage amplitude will vary depending on the pulse width and pacing electrode vector impedance.

If a pace/sense electrode 28 or 30 is included in the pacing electrode vector, resulting in a relatively higher impedance, e.g., in the 400 to 1000 ohm range, the pacing pulse energy delivered may be in the range of 2 to 5 milliJoules. HV therapy circuit 83 may deliver more current via a lower impedance pacing electrode vector, e.g., between defibrillation electrodes 24 and 26, than the current delivered by LV therapy circuit 85 via a pacing electrode vector including pace/sense electrodes 28 or 30 (relatively higher impedance) even when the pacing voltage amplitude is the same. The relatively high pacing pulse amplitude and width required to capture the myocardium by electrodes positioned in an extra-cardiac pacing location may cause extraneous activation of non-cardiac tissue such that the patient perceives the delivery of the pacing pulses and/or experiences discomfort or pain. The high frequency modulation of the pacing pulse signal as disclosed herein is expected to reduce the perception and/or pain experienced by the patient during extra-cardiac pacing pulse delivery by blocking sensory and/or motor nerves that may otherwise be captured by the extra-cardiac pacing pulse.

The HV therapy circuit 83 or the LV therapy circuit 85 may be selected to generate and deliver cardiac pacing pulses using the techniques disclosed herein depending on the pacing capture threshold of the myocardium for a given patient. The HV therapy circuit 83 is configured to deliver CV/DF shock pulses but may be selected by control circuit 80 to deliver pacing pulses, e.g., for delivering ATP, post shock pacing pulses or ventricular pacing pulses during atrio-ventricular conduction block, bradycardia, or asystole. The HV therapy circuit 83 may include a frequency modulator, bias modulator and amplitude modulator as described below for generating a cardiac pacing pulse having modulated high frequency oscillations over the pacing pulse width, which may be modulated between a maximum frequency and a minimum frequency. In this way the HV therapy circuit 83 may generate cardiac electrical stimulation pulse signals that effectively capture the heart but reduce patient discomfort or perception of the pulse signal being delivered. The high frequency content of the pacing pulse is expected to block sensor and/or motor nerves to minimize extraneous activation of non-cardiac tissues.

In response to detecting VT or VF, control circuit 80 may control therapy delivery circuit 84 to deliver therapies such as ATP and/or CV/DF therapy. Therapy, including tachyarrhythmia, bradycardia, asystole and post-shock therapies as examples, can be delivered by initiating charging of high voltage capacitors via a charging circuit, both included in HV therapy circuit 83. Charging is controlled by control circuit 80 which monitors the voltage on the high voltage capacitors, which is passed to control circuit 80 via a charging control line. When the voltage reaches a predetermined value set by control circuit 80, a logic signal is generated on a capacitor full line and passed to therapy delivery circuit 84, terminating charging. A CV/DF or pacing pulse is delivered to the heart 8 under the control of the timing circuit 90 by an output circuit of HV therapy circuit 84 via a control bus. The output circuit may include an output capacitor through which the charged high voltage capacitor is discharged via switching circuitry, e.g., an H-bridge, which determines the electrodes used for delivering the CV/DF or pacing pulse and the pulse wave shape.

Control parameters utilized by control circuit 80 for sensing cardiac events and controlling therapy delivery may be programmed into memory 82 via telemetry circuit 88. Telemetry circuit 88 includes a transceiver and antenna for communicating with external device 40 (shown in FIG. 1A) using RF communication or other communication protocols as described above. Under the control of control circuit 80, telemetry circuit 88 may receive downlink telemetry from and send uplink telemetry to external device 40. In some cases, telemetry circuit 88 may be used to transmit and receive communication signals to/from another medical device implanted in patient 12. Telemetry circuit 88 may receive a pain notification signal from external device 40 in some examples. Control circuit 80 may receive the pain notification signal and adjust electrical stimulation pulse modulation control parameters to reduce pain or sensation of delivered pulse signals.

Figure 4:
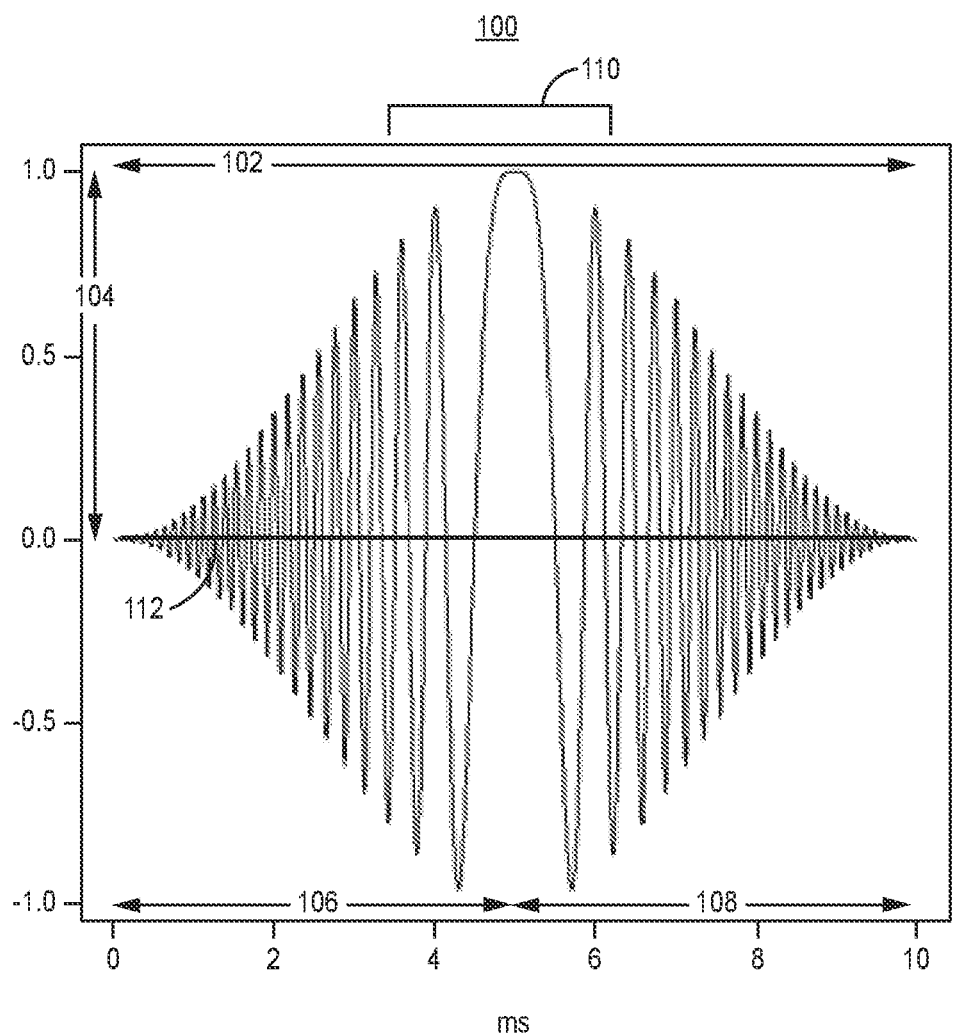
FIG. 4 is a depiction of a frequency modulated pacing pulse generated by the medical device of FIG. 3 according to one example.

FIG. 4 is a depiction of a modulated high frequency pacing pulse signal 100 generated by therapy delivery circuit 84 according to one example. Pulse 100 is shown having an overall pulse width 102 of 10 milliseconds (ms) in this example. The pulse amplitude increases from 0 to a maximum pulse amplitude 104 over the first 50% of the pacing pulse width 102 (5 ms in this example). Pulse amplitude 104 may range, for example between 0.25 Volts and 10 Volts or fall into the other example ranges listed herein. In the various illustrative examples described herein, the pulse signals generated by therapy delivery circuit 84 may be voltage controlled signals where the amplitude of the signals is a voltage amplitude. It is to be understood, however, that in any of the examples presented herein therapy delivery circuit 84 may generate current controlled signals in which case the amplitude of the signals is a current amplitude instead of a voltage amplitude. In either case, the voltage or current amplitude may be modulated by the therapy delivery circuit 84 over the pulse width 102 according to the examples disclosed herein.

In FIG. 4, the amplitude decreases from the maximum amplitude 104 to 0 V over the second 50% of the pulse width 102 (from 5 ms to 10 ms in this example). The bias 112 may be controlled at 0 V by therapy circuit 84. The pacing pulse 100 is biphasic so that the resulting envelope of the amplitude of oscillations of the modulated pacing pulse as shown is sinusoidal. In other examples, the amplitude of the oscillations of the modulated high frequency pacing pulse signal 100 may be fixed over the duration of the pulse width 102 to produce a square pacing pulse signal. In still other examples, the amplitude of the oscillations may be modulated or adjusted over the pulse width 102 to produce a variety of pulse shapes including triangular, saw tooth, stepped up, stepped down, ramped up, ramped down, sinusoidal or any combination thereof as examples.

Therapy delivery circuit 84 modulates the frequency of pacing pulse 100 by decreasing the frequency from a starting frequency to a minimum frequency, which may be 50 Hz or less and may approach 0 Hz in some examples. The frequency of oscillations of pulse signal 110 is decreased over the first portion 106 of the pulse width 102, which may be half of pulse width 102, from 0 to 5 ms in this example. Therapy delivery circuit 84 increases the frequency of oscillations from the minimum frequency to an ending frequency over the second portion 108 of the pulse width 102, which may be the second half of pulse width 102 from 5 ms to 10 ms in this example. The starting frequency of oscillations at the beginning of pulse width 102 (0 ms) may be in the range of 500 Hz to 5000 kHz in various examples. In some examples, the starting frequency is in the range of 1 k Hz to 10 kHz and may be 2.5 kHz or 5 kHz, as examples. The ending frequency at the expiration of pulse width 102 (10 ms in this example) may equal the starting frequency but not necessarily. The ending frequency may be equal to, higher or lower than the starting frequency. Both the starting frequency and the ending frequency are greater than the minimum frequency reached during the pacing pulse width 102 in some examples. At least one of the starting frequency or the ending frequency may be the maximum frequency during the pacing pulse 100. The starting frequency at the beginning of pulse width 102 may be the maximum frequency that is decreased to the minimum frequency during pulse width 102 and the frequency may or may not be increased again after reaching the minimum frequency. In some examples as described below in conjunction with FIG. 10, the ending frequency may be the minimum frequency during the pulse width 102.

Pacing pulse signal 100 is shown to be symmetric over the mid-point of pulse width 102 in the example of FIG. 4, however, the first portion 106 of pulse width 102 over which the pulse frequency is decreased from the starting frequency to the minimum frequency is not required to be the first half of the pulse width 102 as shown. In other examples, therapy delivery circuit 84 may decrease the frequency from the starting frequency to the minimum frequency over a first portion 106 of pulse width 102 that is greater than or less than half of the pulse width 102. Therapy delivery circuit 84 may increase the frequency from the minimum frequency to the ending frequency over the remaining second portion 108 of pulse width 102, which may be less than or greater than half of the pulse width 102 depending on the duration of the first portion 106.

The high frequency oscillations of pulse signal 100 during the first portion 106 are delivered to block motor and/or sensory nerves that may otherwise be activated by a pacing pulse, causing pain or other sensation. As the starting high frequency of oscillations decreases over the first portion 106 and the pulse amplitude increases, the net delivered charge of pacing pulse signal 100 reaches a cardiac capture threshold for causing depolarization of the myocardium. The minimum frequency may occur at a time during pulse width 102 that corresponds to maximum pulse amplitude 104, as indicated by the low frequency, high amplitude portion 110 of pulse signal 100. The minimum frequency and the maximum pulse amplitude 104 may be reached concurrently during pulse width 102, which may or may not be at the midpoint of pulse width 102 as shown here. By decreasing the frequency from a starting high frequency, e.g., greater than 1 kHz or more, to a minimum frequency, e.g., 50 Hz or less, the decreasing frequency (and increasing the pulse amplitude in this example), pulse signal produces a charge accumulation such that delivered current increases as the frequency decreases until myocardial capture occurs. After myocardial capture occurs, the frequency may increase again (with decreasing amplitude in this example).

In some examples, the modulated high frequency pulse signal may be followed by a recharge pulse, which is a secondary pulse that causes an equal amount of charge to flow in the opposite direction of the modulated high frequency pulse signal. The charge in the recharge pulse is intended to equal the amount of charge in the therapeutic modulated high frequency pulse signal to minimize charge accumulation at the electrode surface over time. Charge accumulation at the electrode-tissue interface over time can lead to chemical reactions at the electrode-tissue interface, potentially causing tissue and/or electrode damage over time.

The therapeutic modulated high frequency of pacing pulse signal 100 is expected to reduce perception and/or discomfort to the patient during delivery of pacing pulse signal 100 to capture the patient's heart. The starting and/or ending frequency may be selected so that the high frequency content of pacing pulse signal 100 blocks sensory and/or motor nerves to minimize or avoid activation of sensory and/or motor nerves while still capturing the myocardium by the low frequency portion 110 of the pacing pulse signal 100. Pulse signal 100 includes low frequency content during portion 110 having a pulse amplitude within pulse width 102 that meets or exceeds the myocardial capture threshold.

While the maximum pulse amplitude 104 (and peak-to-peak amplitude of twice the maximum pulse amplitude 104) occurs at a midpoint of the pulse width 102 in the example shown, the maximum pulse amplitude 104 may occur earlier than the midpoint and may be held for a portion of the pulse width 102, e.g., in a ramped square wave. In other examples, the maximum pulse amplitude 104 may be reached earlier in the first portion 106 and begin to decrease before the midpoint of pulse width 102. In some cases, the maximum pulse amplitude 104 may be reached during a relatively high frequency portion of the pulse signal 100, e.g., earlier in portion 106, to promote blocking of sensory and/or motor nerves before the low frequency portion 110 of pulse signal 100, particularly when a high amplitude is needed to capture the myocardium during the low frequency portion 110. In some examples, the maximum peak amplitude 104 of the pulse signal 100 may be reached before the minimum frequency is reached and be held at the maximum pulse amplitude through the minimum frequency portion until the frequency increases again. In other examples, the maximum pulse amplitude may be held at the maximum until the expiration of pulse width 102 or decrease to a lower pulse amplitude during the low frequency portion 110 that captures the myocardium. The pulse amplitude may or may not be at a maximum during the low frequency portion 110 but is at least high enough during the low frequency portion 110 of pulse signal 100 to capture the myocardium to evoke a depolarization.

Figure 5:
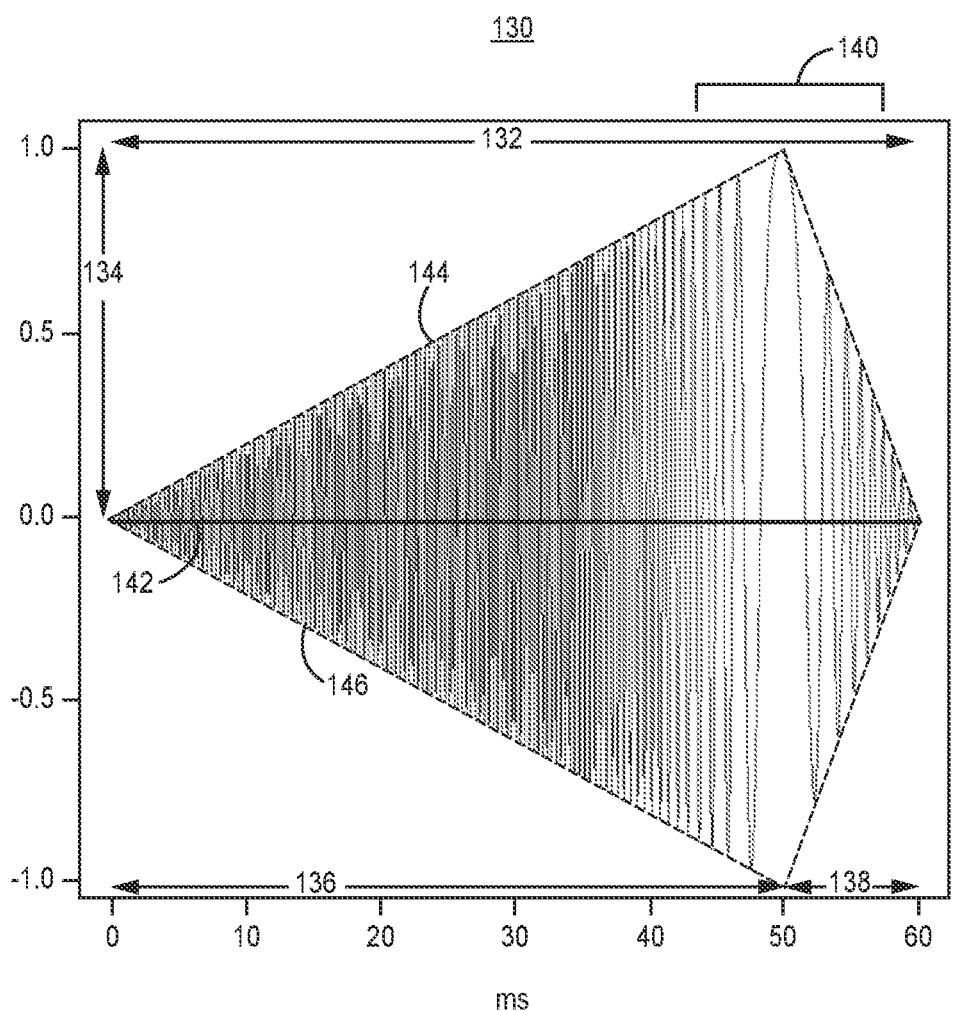
FIG. 5 is a depiction of a frequency modulated pacing pulse generated by the medical device of FIG. 3 according to another example.

FIG. 5 is a depiction of a modulated high frequency pacing pulse signal 130 generated by therapy delivery circuit 84 of FIG. 3 according to another example. Pulse signal 130 has an overall pulse width 132, shown as 60 milliseconds (ms) in this example though the pulse width may be shorter according to any of the example ranges given herein. The modulated high frequency pacing pulse signals generated by therapy delivery circuit 84 may have a pulse width of 1 ms or less or up to 60 ms or more in various examples. The duration of the pulse width may depend on the pulse energy required for capturing tissue for a particular therapy application and the therapy delivery circuit being used to generate the pulse signal. In some examples, the pulse width is in the range of 0.02 ms to 1.2 ms. In other examples, the pulse width is in the range of 1 ms to 10 ms. In other examples the pulse width is in the range of 10 ms to 40 ms. In still other examples, the pulse width is in the range of 30 ms to 60 ms.

The frequency of oscillations of pulse signal 130 decreases from a high frequency at the starting time of pulse width 132 (0 ms) down to a minimum frequency, which may approach 0 Hz, over a first, decreasing frequency portion 136 of the pulse width 132. The frequency may effectively be 0 Hz at its minimum though a true 0 Hz signal may not be reached due to constraints of the pulse generation circuitry. The minimum frequency may be less than or equal to 100 Hz, less than or equal to 50 Hz, less than or equal to 20 Hz, less than or equal to 10 Hz, less than or equal to 5 Hz, less than or equal to 1 Hz or as low as 0.1 Hz in various examples. The frequency increases from the minimum frequency over the second, increasing frequency portion 138 until the expiration of the pulse width 132. The decreasing frequency portion 136 may be greater than the second increasing frequency portion 138 of pulse width 132. The second, increasing frequency portion 138 is 20% of the first, decreasing portion 136 in the example shown. However, the second portion 138 may be any percentage of the first portion 136 or of the overall pulse width 132.

The first, decreasing frequency portion 136 may be at least 50% or more (up to 100%) of the pulse width 132 to promote nerve blocking and minimized perception or discomfort caused by the pacing pulse signal during the high amplitude, low frequency portion 140 by delivering the high frequency while the pulse amplitude is low and increased until the maximum pulse amplitude 134 is reached. However the first, decreasing frequency portion 136 may be less than 50% of the pulse width in other examples. In one example, the first portion 136 is between 10% and 30% of the pulse width 132, and the second portion 138 is between 90% and 70% of the pulse width. In another example, the first portion is between 30% and 50% of the pulse width, and the second portion is between 70% and 50% of the pulse width. In still another example, the first portion is between 50% and 100% and the second portion is between 0% (no increasing frequency portion) and 50% of the pulse width 132. These ranges are provided as examples with no limitation intended.

The ending frequency reached at the expiration of the pulse width 132 may be less than the starting frequency at the beginning of the pulse width 132 since the increasing frequency portion 138 is shorter than the decreasing frequency portion 136. In the example shown the rate of decreasing the frequency over the first portion 136 may be equal in magnitude to the rate of increasing the frequency over the second portion 138. However since the second portion 138 is shorter in duration than the first portion 136, the ending frequency is lower than the starting frequency at the beginning of pulse width 132. In other examples, the rate of increasing the frequency may be greater than the rate of decreasing the frequency such that the frequency is increased more rapidly over the second portion 138 of the pulse width 132. The final frequency at the expiration of the pulse width 132 may be less than or equal to the starting frequency in this case. In some cases, the ending frequency may be greater than the starting frequency.

The pulse amplitude of the oscillations of pulse signal 130 increases from zero to a maximum pulse amplitude 134 over the first, decreasing frequency portion 136 of the pacing pulse width 132 in this example and decreases from the maximum pulse amplitude 134 to zero over the second, increasing frequency portion 138 of the pulse width 132 (from 50 ms to 60 ms in this example). The pacing pulse signal 130 is biphasic with a bias 142 controlled at a zero amplitude. The resulting maximum amplitude envelope 144 of oscillations of the modulated high frequency pacing pulse signal 130 and the minimum amplitude envelope 146 of the oscillations are both triangular in shape. Other shapes of a modulated high frequency pacing pulse signal having a first, decreasing frequency portion 136 and an optional second increasing frequency portion 138 are possible, however. The sinusoidal and triangular shapes shown in FIG. 4 and FIG. 5, respectively, are shown as examples with no limitations intended pertaining to the amplitude modulation of pulse signals 100 and 130 over the respective pulse widths 102 and 132. The maximum pulse amplitude 104 or 134 occurs near or coincides with the minimum frequency of the pulse 100 or 130 such that the high amplitude, low frequency portion (portion 110 in FIG. 4 and portion 140 in FIG. 5) of the pacing pulse signal captures the myocardium. In other examples, the pulse amplitude may be modulated or adjusted up to the maximum amplitude 134 over the first, decreasing frequency portion 136 using step changes or other non-linear rates of change rather than the constant rate of change as shown.

The amplitude of pulse 130 decreases at a faster rate over the second, increasing frequency portion 138 than the rate of amplitude increase over the first, decreasing frequency portion 136. As a result, the amplitude is shown to fall from the maximum pulse amplitude 134 to zero by the end of the shorter, second portion 138. However, the rates of change in amplitude over the first portion 136 and the second portion 138 may be the same or different in various examples. The rate of decreasing pulse amplitude may be slower than shown such that the ending pulse amplitude of the high frequency oscillations at the expiration of pulse width 132 may be greater than 0. In other examples, the pulse amplitude may remain constant over the duration of the second portion 138 at the maximum pulse amplitude 134 until the expiration of the pulse width 132. In this case, only frequency is modulated over the second portion 138 of pulse width 132.

Figure 6:
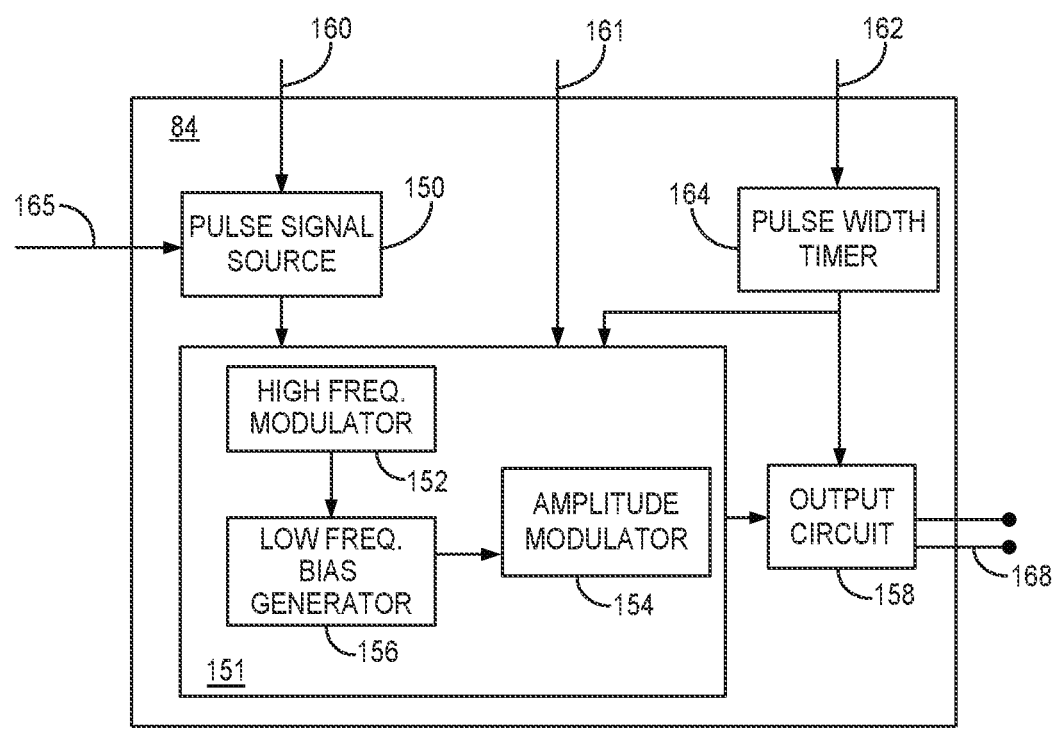
FIG. 6 is a conceptual diagram of the therapy delivery circuit of the medical device of FIG. 3 according to one example.

FIG. 6 is a conceptual diagram of therapy delivery circuit 84 according to one example. As described above, therapy delivery circuit 84 may include a HV therapy circuit 83 and a LV therapy circuit 85 in some examples. In other examples, therapy delivery circuit 84 may include HV therapy circuit 83 without LV therapy circuit 85 or LV therapy circuit 85 without HV therapy circuit 83. The components shown in FIG. 6, e.g., signal source 150, modulator 151, pulse width timer 164, and output circuit 158 may correspond to components included in HV therapy circuit 83 and/or LV therapy circuit 85. In some examples, some components shown in FIG. 6 may be included in both HV therapy circuit 83 and LV therapy circuit 85 or shared between HV therapy circuit 83 and LV therapy circuit 85. The HV therapy circuit 83 or the LV therapy circuit 85 components and associated functionality may be represented by the components shown in FIG. 6. Thus, HV therapy circuit 83 and/or LV therapy circuit 85 may be configured to generate electrical stimulation pulse signals using the modulation techniques disclosed herein. In some examples, the electrical stimulation pulse signals are relatively low energy cardiac pacing pulses (generated by LV therapy circuit 85 or HV therapy circuit 83) for pacing the patient's heart at a desired rate. In other examples, the cardiac electrical stimulation signals are high energy cardioversion/defibrillation pulses generated by HV therapy circuit 83 for terminating a tachyarrhythmia, e.g., a fast tachycardia or fibrillation.

Therapy delivery circuit 84 includes a pulse signal source 150 that receives power on line 165 from power source 98 of ICD 14. Pulse signal source 150 may be a voltage controlled signal source or a current controlled signal source. Pulse signal source 150 receives a pace timing signal 160 from control circuit 80. Pulse signal source 150 may respond to the pace timing signal 160 by starting a pulse signal that is passed to modulator 151. In some examples, signal source 150 includes a charging circuit and one or more holding capacitors or other charge storage devices that are charged by the charging circuit to a voltage required to generate an electrical stimulation pulse signal having a desired maximum pulse amplitude, e.g., maximum pulse amplitude 104 shown in FIG. 4. The holding capacitor(s) may be charged before receiving the pace timing signal 160, e.g., during a pacing (or other stimulation) interval, or in response to receiving the pace timing signal 160. As described above, when signal source 150 is included in HV therapy circuit 83, the signal source 150 may include a transformer (coupled to power source 98) and one or more high voltage capacitors that are charged to a desired voltage under the control of a processor. The high voltage capacitors may include two or three high voltage capacitors in series having an effective capacitance of 148 to 155 microfarads in one example.

When pulse signal source 150 is included in LV therapy circuit 85, pulse signal source 150 may include a state machine and one or more low voltage holding capacitors. Pulse signal source 150 may be configured to charge the low voltage holding capacitor(s) to a multiple of the voltage of a battery included in power source 98 without requiring a transformer. Pulse signal source 150 may include one or more low voltage capacitors each having a capacitance of up to 6 microfarads, up to 10 microfarads, up to 20 microfarads or other selected capacitance, but all have a capacitance significantly less than the effective capacitance of the high voltage capacitors included in HV therapy circuit 83. The low voltage holding capacitors included in LV therapy circuit 85 may have a lower breakdown voltage than the high voltage holding capacitors of HV therapy circuit 83, allowing the high voltage capacitor(s) to be charged to a shock voltage amplitude, e.g., 100 V or more, required for delivering CV/DF shocks.

In response to pace timing signal 160, pulse signal source 150 may pass a signal to modulator 151 for generating a high frequency electrical stimulation pulse signal, e.g., a cardiac pacing pulse, which is delivered via a selected electrode vector 168. The electrode vector 168 may be selected from any available electrodes, e.g., electrodes 24, 26, 28, 30 and/or housing 15 as shown in FIGS. 1A and 2A. The signal from pulse signal source 150 is passed to output circuit 158 via modulator 151, which may provide high frequency modulation by high frequency modulator 152, bias modulation by low frequency bias generator 156 and/or amplitude modulation by amplitude modulator 154. In one example, modulator 151 includes a high frequency modulator 152 configured to modulate the signal from pulse signal source 150 from a starting frequency down to a minimum frequency and may increase the frequency from the minimum frequency to an ending frequency during a pulse width as described above in conjunction with FIGS. 4 and 5. High frequency modulator 152 may modulate the frequency of oscillations of the pulse signal according to frequency modulation control parameters, which may be received from control signal 161 passed to modulator 151 from control circuit 80.

In some examples, the starting frequency is the maximum frequency of the pulse signal. The ending frequency may equal the maximum frequency of the pulse signal. The starting frequency and the ending frequency may be the same frequency in some examples. In other examples, high frequency modulator 152 may modulate the frequency of the pulse signal from a starting frequency up to a first maximum frequency greater than the starting frequency and from the first maximum frequency down to the minimum frequency over a first portion of the pulse width. In some examples, high frequency modulator 152 modulates the frequency of the pulse signal from the minimum frequency up to a second maximum frequency greater than the ending frequency and from the second maximum frequency down to the ending frequency over a second portion of the pulse width. The starting and ending frequencies may or may not be the same frequencies. The first maximum frequency and the second maximum frequency may or may not be the same frequencies.

Therapy delivery circuit 84 may include a pulse width timer 164 that receives a pacing pulse width signal 162, which may provide timing signals to the high frequency modulator 152, low frequency bias generator 156 and amplitude modulator 154. For example, timing signals from pulse width timer 164 may be used by high frequency modulator 152 to control the time intervals of decreasing and increasing frequency over one or more portions of the pulse width, e.g., over the first portion and second portion of the pulse width as shown in FIGS. 4 and 5. In some examples, the high frequency modulator 152 maintains a constant high frequency carrier signal throughout the pulse width without modulating between minimum and maximum frequencies. In these examples, the low frequency bias generator 156 may be enabled to modulate the bias of the high frequency signal to produce a pulse signal that results in a net charge accumulation at the electrode vector 168 over the pulse width that results in a net current flow that captures the myocardium (or another targeted tissue).

Modulator 151 may include low frequency bias generator 156 to modulate the bias of the high frequency signal, which may include frequency modulation or a constant high frequency during the pulse width. Low frequency bias generator 156 may be configured to hold the bias of the high frequency signal received from high frequency modulator 152 at a constant offset, e.g., a 0 offset, as shown in the examples of FIGS. 4 and 5. In other examples, low frequency bias generator 156 may slowly modulate the bias of the high frequency pulse signal received from high frequency modulator 152 to cause a charge imbalance to accumulate such that myocardial pacing capture occurs during the pacing pulse signal. Examples of pulse signals that include bias modulation are described below in conjunction with the example pulse signals shown in FIGS. 7 and 8.

The high frequency pacing pulse signal received from high frequency modulator 152 may or may not be frequency modulated during the pulse width when the low frequency bias generator 156 modulates the bias of the high frequency pulse signal. As discussed below, the high frequency modulator 152 may output a fixed frequency signal, e.g., a 2.5 kHz or 5.0 kHz signal for the duration of the pulse width when low frequency bias generator 156 is configured to modulate the bias. The bias may be modulated between a minimum offset, e.g., 0 offset, and a maximum offset during the pulse width. The bias may be modulated according to a low frequency cutoff that controls how long the bias is maintained at an offset value (without significant decay) and a high frequency cutoff that controls how often the offset is adjusted from one value to another. For example, the bias may be held constant, e.g., at a zero offset, by low frequency bias generator setting the low frequency cutoff to 0 Hz based on a control signal 161 from control circuit 80. The offset may be adjusted by low frequency bias generator 156 as often as every 1 ms by setting the high frequency cutoff to 1 kHz, as an example. Low frequency bias generator 156 may modulate the bias according to bias modulation control parameters included in control signal 161 by adjusting the offset of the signal bias according to a specified timing or frequency intervals. The bias of the high frequency signal may be modulated to have a sinusoidal, square, ramped or other desired shape to contribute to a net charge accumulation at electrode vector 168 during the pulse signal. Control signal 161 from control circuit 80 may include bias modulation control parameters used by low frequency bias generator 156 to control the minimum offset, maximum offset, rate of change (increase and/or decrease) of the offset, number of low frequency oscillations of the bias during the pulse width, the width of each oscillation, amplitude of each oscillation, and/or time intervals of constant offset, which may be zero offset or non-zero offset, as examples of bias control parameters.

In some examples, therapy delivery circuit 84 includes an amplitude modulator 154. Amplitude modulator 154 may receive the high frequency signal, which may be a frequency modulated and/or bias modulated signal. Amplitude modulator 154 may modulate the pulse amplitude of the received signal to generate the output pulse signal having a desired maximum pulse amplitude and a desired envelope or shape defined by the amplitudes of the oscillations of the pulse signal. Amplitude modulator 154 may receive amplitude modulation control parameters from control signal 161 from control circuit 80 including amplitude control parameters used for controlling the rate of change and minimum and maximum amplitudes of the oscillations of the high frequency signal received from low frequency bias generator 156 (or from high frequency modulator 152 in some examples). Amplitude modulator 154 may also receive a signal from pulse width timer 164 for controlling the time over which amplitude modulator 154 adjusts the amplitude of the oscillations of the pulse signal so that, for example, the maximum pulse amplitude occurs during the pulse width at a specified time, which may coincide with a minimum frequency, a maximum bias offset or other feature of the high frequency signal received from low frequency bias generator 156.

A variety of pulse shapes may be generated by amplitude modulator 154, such as square, triangular, saw tooth, ramped, stepped, and sinusoidal as examples. The amplitude modulator 154 may be configured to adjust the amplitude from a starting pulse amplitude up to a maximum pulse amplitude over a first portion of the pulse width and adjust the pulse amplitude from the maximum pulse amplitude to an ending pulse amplitude over a second portion of the pulse width. Amplitude modulator 154 may receive timing signals from pulse width timer 164 for controlling the timing of the amplitude modulation over the pulse width. For example, the amplitude modulator 154 may be configured to modulate the amplitude to a maximum pulse amplitude that coincides in time with the minimum frequency of the pulse signal such that the net charge accumulation results in capture of the myocardium during the pulse signal. In other examples, amplitude modulator 154 modulates the pulse amplitude to reach a maximum pulse amplitude corresponding in time to a maximum offset of the bias. However, the maximum amplitude of the pulse signal may be reached before or after the minimum frequency and/or maximum bias offset. The maximum pulse amplitude may occur within a time interval, e.g., within time interval 110 in FIG. 4, of the minimum frequency and/or a maximum bias offset so that the pulse energy within a portion of the pulse signal equals or exceeds the energy required to capture the myocardium and cause a depolarization.

In some cases, amplitude modulator 154 may hold the amplitude of oscillations of the pulse signal at a constant maximum pulse amplitude for all or a portion of the pulse width. The pulse signal generated by modulator 151 may correspond to any of the example pulse signals described herein and/or shown in the accompanying drawings, each including modulation of the high frequency oscillations between a minimum and maximum frequency and/or modulation of the bias between a minimum and maximum offset in order to accumulate a net charge at the electrode vector 168 during the pulse signal that captures the myocardium.

The pulse width timer 164 may pass a pulse width timing signal to output circuit 158 to control the closing and opening of switches included in output circuit 158 for coupling the output of modulator 151 to electrode vector 168. Output circuit 158 includes switching circuitry configured to couple the modulated high frequency pulse signal to the selected electrode vector 168 for the duration of the pacing pulse width as controlled by pulse width timer 164. The output circuit 158 may include one or more switches that couple the output of modulator 151 to the selected electrode vector 168 via switching circuitry, e.g., an H-bridge or a combination of switches and diodes. Switches included in output circuit 158 may be implemented as silicon-controlled rectifiers (SCRs), insulated-gate bipolar transistors (IGBTs), metal-oxide-semiconductor field-effect transistors (MOSFETs), and/or other switching circuit components or combinations thereof.

Figure 7:
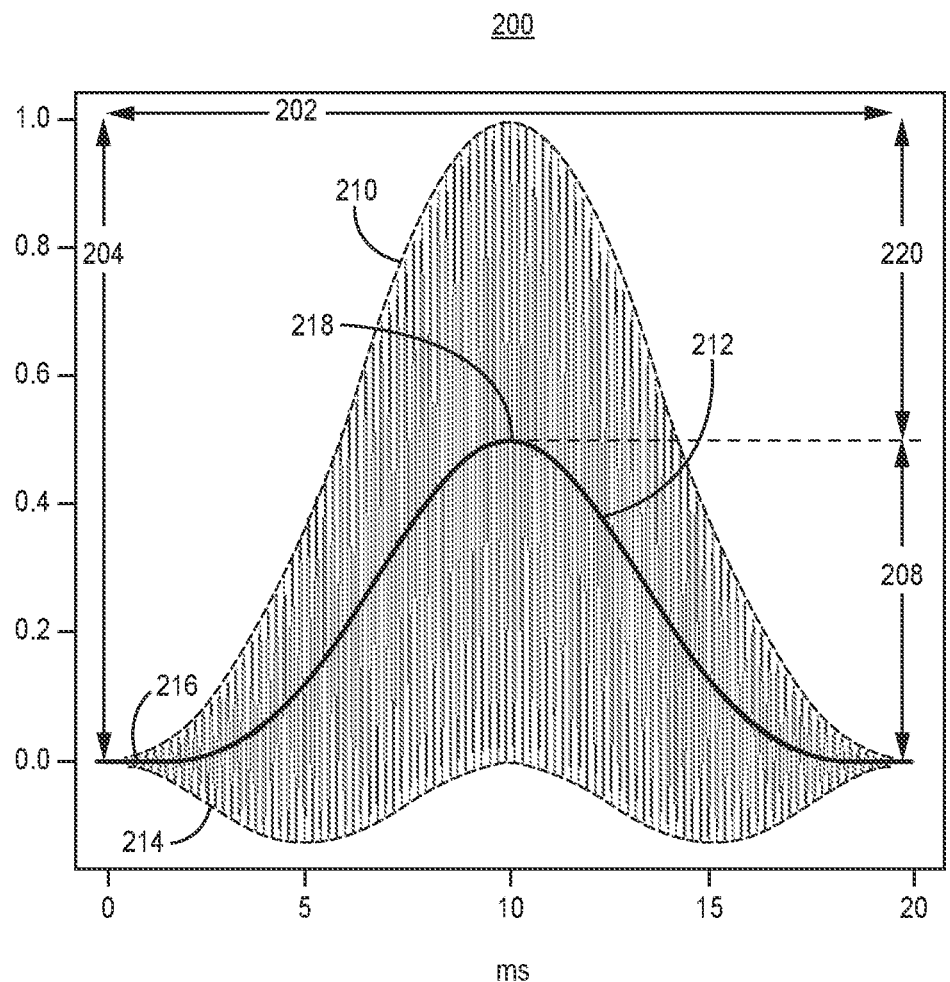
FIG. 7 is a depiction of a pacing pulse signal that may be generated by the therapy delivery circuit of FIG. 6 according to one example.

FIG. 7 is a depiction of an electrical stimulation pulse signal 200 that may be generated by therapy delivery circuit 84 according to another example. Pulse signal 200 may be a cardiac pacing pulse or CV/DF shock pulse, as examples. With continued reference to FIG. 6, the high frequency modulator 152 may generate a high frequency signal, e.g., 2.5 kHz, 5 kHz or other selected frequency. In this example, the high frequency oscillations of the pulse signal 200 have a constant frequency. The amplitude modulator 154 may modulate the amplitude of the high frequency oscillations from a starting minimum pulse amplitude, which may be 0 Volts, to a maximum amplitude 220 and back down to an ending amplitude, e.g., back to 0 Volts, over pulse width 202. The modulation of the amplitude of the oscillations of the high frequency pulse signal 200 in this example produces a sinusoidal envelope 210 of the maximum amplitudes of the oscillations of the pulse signal 200.

The low frequency bias generator 156 may modulate the bias 212 of the high frequency signal at a low frequency of modulation over pulse width 202. For example, the bias 212 may be modulated from a starting minimum offset 216, e.g., at 0 Volts, to a maximum offset 218 over an offset range 208. In this example the maximum offset 218 may have an amplitude up to 100% of the maximum pulse amplitude 220 of the high frequency oscillations of the pacing pulse 200. In other examples, the maximum offset 218 may be greater than or less than the maximum pulse amplitude 220 of the high frequency oscillations. Depending on the rate of increasing the bias 212 and the rate of increasing the pulse amplitude, the offset of the bias 212 may at times be greater than the pulse amplitude of the high frequency oscillations during the pulse width and at other times be less than or equal to the pulse amplitude of the high frequency oscillations of the pulse signal. The maximum pulse amplitude 220 of the high frequency oscillations coincides in time with the maximum offset 218 in this example, resulting in an overall maximum peak-to-peak amplitude 204 of the pulse signal 200.

Low frequency bias generator 256 may adjust the offset of the pulse signal 200 as frequently as every 1 ms to generate a bias 212 of any desired shape and rates of change over the pulse width 202. In the example shown, the frequency of oscillation of the bias 212 between the minimum starting offset 216 and the maximum offset 218 may correspond to a low frequency, 50 Hz as an example, during this 20 ms pulse width 202. This low frequency modulation of the bias 212 causes charge accumulation during the pulse signal 200 that results in myocardial capture during the pulse signal 200 and subsequent myocardial depolarization. In this case, the charge accumulation during pulse signal 200 is caused by the low frequency modulation of the bias 212 of pulse signal 200 without requiring frequency modulation of the high frequency oscillations of pulse signal 200. The bias 212 of pulse signal 200 may be modulated at a frequency of 2 Hz to 500 Hz in various examples, with no limitation intended, and is modulated at a frequency of 10 Hz to 300 Hz in some examples. The frequency of the bias modulation oscillations may be selected in part based on the pulse width 202. For a relatively short pulse width 202, a relatively higher frequency of modulation of the bias 212 may be used to promote at least a quarter cycle, at least a half cycle, at least one cycle, or multiple cycles, e.g., up to four cycles, of the bias oscillations between a minimum offset and a maximum offset during the pulse width 202. The modulation of the bias 212 causes the minimum amplitude envelope 214 of the high frequency oscillations to have a sinusoidal shape that is different than the maximum amplitude envelope 210.

Figure 8:
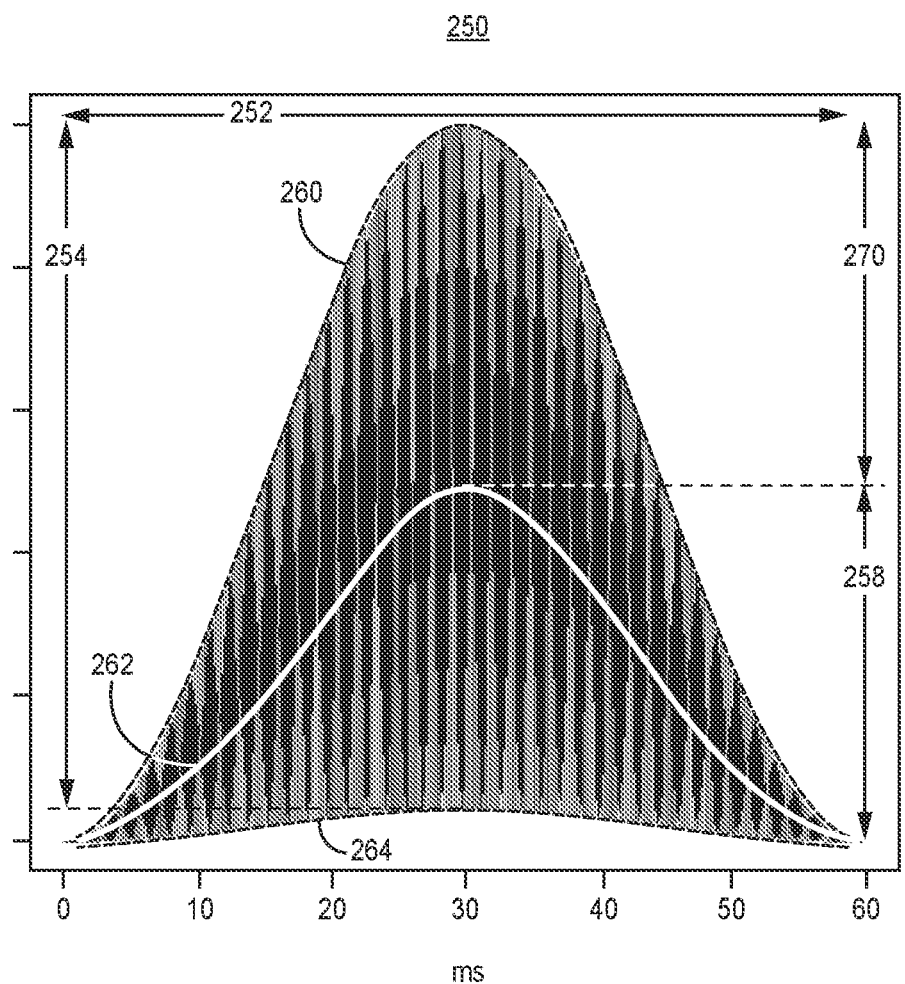
FIG. 8 is a depiction of a pacing pulse signal that may be generated by the therapy delivery circuit of FIG. 6 according to another example.

The charge accumulation that causes myocardial capture during pulse signal 100 of FIG. 4 or pulse signal 130 of FIG. 5 is generated by the high frequency modulation performed by high frequency modulator 152. The charge accumulation that causes capture during the pulse signal 200 of FIG. 7 and the pulse signal 250 of FIG. 8 (described below) is caused by the low frequency bias modulation performed by low frequency bias generator 156. Accordingly, in some examples high frequency modulator 152 may be configured to generate a fixed high frequency signal without frequency modulation, and low frequency bias generator 156 may be configured to generate a low frequency bias changes to generate an electrical stimulation pulse that captures the myocardium and reduces patient perception and/or discomfort produced by the pulse delivery compared to an electrical stimulation pulse that does not include high frequency oscillations. In other examples, high frequency modulator 152 is configured to modulate the high frequency from a starting frequency down to a minimum frequency, and the low frequency bias generator 156 may be optional or may be configured to maintain a constant offset, e.g., 0 offset, of the high frequency signal generated by high frequency modulator 152 as shown in FIGS. 4 and 5. In still other examples, therapy delivery circuit 84 may be configured to generate an electrical stimulation pulse signal that includes a combination both high frequency modulation (e.g., as shown in FIGS. 4 and 5) and low frequency bias modulation (e.g., as shown in FIGS. 7 and 8). In each of these cases, amplitude modulation by amplitude modulator 154 may or may not be performed. The high frequency modulated and/or low frequency bias modulated signal may have a fixed pulse amplitude for the entire duration of the pulse width in some examples.

FIG. 8 is a depiction of a modulated electrical stimulation pulse signal 250 that may be generated by therapy delivery circuit 84 according to another example. The high frequency modulator 152 may generate a constant high frequency signal, e.g., 2.5 kHz, 5 kHz or other selected frequency, which may be between 1 kHz and 10 kHz with no limitation intended. The amplitude modulator 154 may modulate the pulse amplitude of the high frequency oscillations from a starting amplitude, which may be 0 Volts, to a maximum pulse amplitude 270 (with maximum peak-to-peak amplitude 254) and back down to the ending amplitude, e.g., back to 0 Volts or a value greater than 0 Volts, over pulse width 252 to produce a generally sinusoidal maximum amplitude envelope 260 of the pulse signal 250. The maximum envelope 260 of pulse signal 250 may be shaped differently than shown in FIG. 8 by different modulation of the pulse amplitude of the high frequency oscillations by amplitude modulator 154, which may be according to any of the examples given herein.

The low frequency bias generator 156 may modulate the bias 262 of the high frequency signal over pulse width 252. The bias 262 may start at a minimum offset, e.g., 0 V, and be modulated to a maximum offset 258, which may be equal to the maximum pulse amplitude 270 of the high frequency oscillations in some examples. In this example, the minimum amplitude envelope 264 of the high frequency oscillations is observed to increase from a minimum of 0 V to a maximum amplitude aligned with the maximum peak-to-peak amplitude 254 and back to the minimum offset of 0 V over the pulse width 252. Compared to the minimum amplitude envelope 214 of the pulse signal 200 shown in FIG. 7, the different shape of the minimum amplitude envelope 264 is achieved by different rates of increasing and decreasing the offset by low frequency bias generator 256 than the rates of increasing and decreasing the pulse amplitude by amplitude modulator 154. For example, the initial rate of increasing the bias offset is greater than the initial rate of increasing the pulse amplitude such that the minimum amplitude envelope never falls below 0 V.

In this example, the bias 262 may be modulated to produce 5 to 20 Hz oscillations, e.g., one 16 Hz oscillation as shown, of the bias over the 60 ms pulse width. The minimum amplitude envelope 264 remains positive in polarity without going negative by controlling the rate of increase of the bias 262 and the rate of increasing amplitude of the pulse signal. In the example shown, the pulse width 252 is 60 ms allowing a relatively low rate of change of the bias 262 over the relatively long pulse width 252. Charge accumulation is expected to occur as the pulse signal 250 reaches the maximum peak-to-peak amplitude 254, resulting in myocardial capture.

In other examples, depending on the rate of changing the bias offset and the resulting frequency of oscillations of the bias 262 and depending on the rate of the amplitude modulation applied by amplitude modulator 154, the maximum bias offset 258 may be but is not necessarily aligned with the maximum pulse amplitude 270 of the high frequency oscillations as shown in FIGS. 7 and 8. While only one oscillation from the minimum offset to the maximum offset back to the minimum offset is shown in FIGS. 7 and 8, the number of oscillations of the bias between a minimum and maximum offset may be one, two, three, four or other selected number of oscillations. A different frequency of oscillations of the bias 262 than the rate of amplitude modulation may result in a different number of peaks of the maximum amplitude envelope 260 (only one in FIG. 8) than the number of peaks of the minimum amplitude envelope 264. Accordingly the maximum amplitude envelope 260 of the pulse signal 250 and the minimum amplitude envelope 264 may be different from each other in bias modulated pulse signals as shown in the examples of FIGS. 7 and 8. This difference contributes to charge accumulation during the pulse signal 200 or 250 for achieving myocardial capture during the pulse width 252 while the high frequency oscillations act to reduce patient pain and sensation of the pulse signal delivery.

The modulation of the bias produced by low frequency bias generator 156 is shown as generally sinusoidal in the examples of FIGS. 7 and 8. In other examples, low frequency bias generator 156 may modulate the bias of a high frequency pulse signal according to other linear or non-linear rates of change which may ramped, saw-tooth or other shapes but occur at a different rate of change than the modulation of the pulse amplitude so that charge accumulation occurs as the pulse signal reaches a maximum pulse amplitude set to capture the myocardium. For example, low frequency bias generator 156 may increase the offset as often as every 1 ms to ramp up the offset to a maximum offset, hold the bias at the maximum offset for a predetermined portion of the pulse width, then adjust the offset back down to a minimum offset to produce a generally square waveform of the bias.

Figure 9:
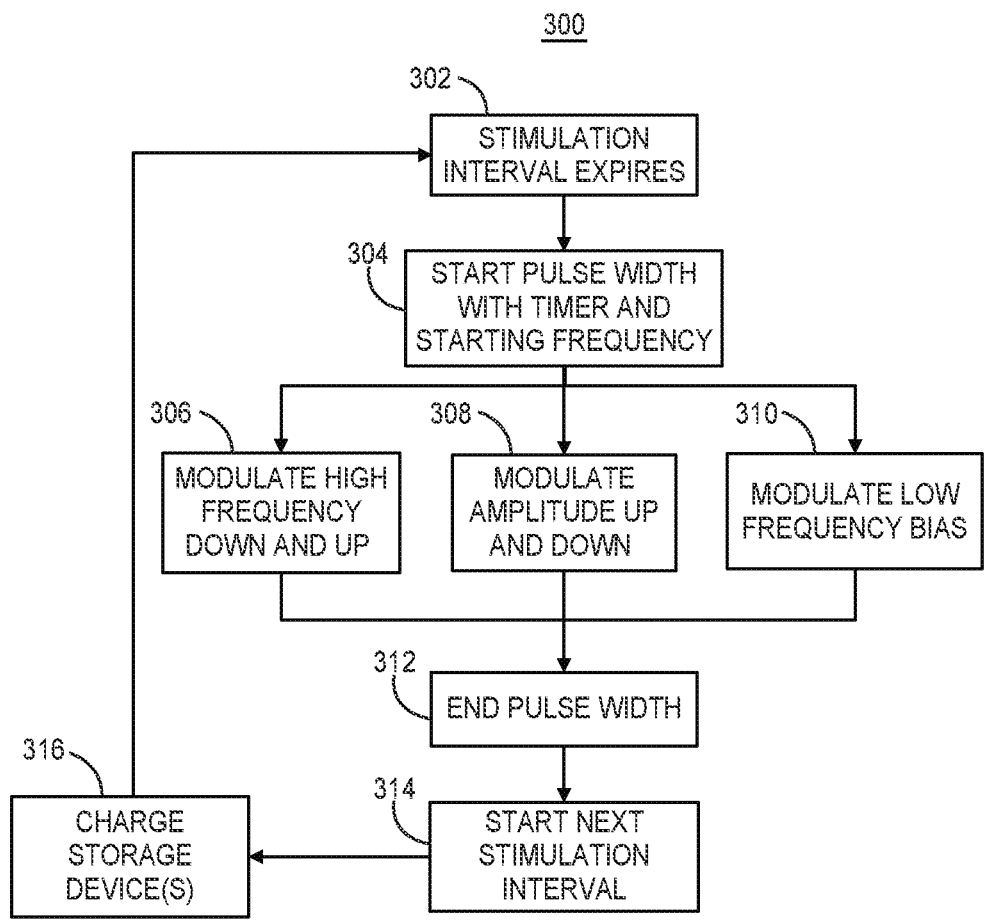
FIG. 9 is a flow chart of a method for generating a therapeutic electrical stimulation pulse by a medical device according to some examples.

FIG. 9 is a flow chart 300 of a method for generating a therapeutic electrical stimulation pulse by a medical device according to one example. At block 302, a stimulation interval expires. The stimulation interval may be a pacing interval set by timing circuit 90 of control circuit 80 shown in FIG. 3. In other medical applications, e.g., neuro or muscle stimulation applications, an inter-pulse interval may expire at block 302 as controlled by a processor or timing circuit of the medical device. The inter-pulse interval may be set to control a rate of stimulating nerves for causing contraction of a muscle, such as skeletal muscle, the diaphragm, or smooth muscle of the digestive tract as examples. A pulse width timer, e.g., pulse width timer 164 of FIG. 6, starts timing the electrical stimulation pulse width at block 304 and may provide timing signals to high frequency modulator 152, amplitude modulator 154, low frequency bias generator 156 and/or output circuit 158 of therapy circuit 84. In cardiac pacing applications, the pulse width is the cardiac pacing pulse width and may be less than 1 ms or up to 60 ms in duration, as examples, with no limitation intended. The pacing pulse width may be 5 ms to 20 ms in some examples and is 10 ms in one example. In other therapeutic electrical stimulation applications, the pulse width timer is set to a pulse width or duration of the electrical stimulation pulse signal, which may be in the example ranges given above or longer or shorter than the examples given above depending on the energy required to depolarize the targeted tissue and achieve a desired response (e.g., activation or contraction of the nerve or muscle) and depending on the duration of the high frequency portion of the pulse signal required to reduce pain or sensation due to extraneous stimulation.

A signal source 150 of the therapy delivery circuit 84 of FIG. 6 starts the pulse signal at block 304 upon starting the pulse width timer 164. Modulator 151 may modulate the pulse signal starting at a selected high frequency, e.g., 1 to 10 kHz. The pulse signal may be started at 0 pulse amplitude or at another selected starting pulse amplitude, which may be the maximum pulse amplitude. During the pulse width, at block 306 the therapy delivery circuit 84 may modulate the high frequency oscillations of the pulse signal from the starting frequency down to a minimum frequency and back up to an ending frequency according to any of the examples given above. In one example, the high frequency modulator 152 modulates the frequency from 2.5 kHz or 5 kHz down to 0 Hz and back up to 2.5 kHz or 5 kHz. In other examples, high frequency modulator 152 maintains a fixed high frequency throughout the pulse width and low frequency bias generator 156 modulates the bias to produce low frequency oscillations of the bias offset, e.g., 500 Hz or less, at block 310. At block 308, amplitude modulator 154 may modulate the amplitude of the pulse signal over the pulse width according to any of the examples given above. In other examples, the amplitude of the pulse signal is fixed during the pulse width (though some amplitude decay may occur over the pulse width, e.g., according to the RC time constant of the pacing output circuit and pacing electrode impedance).

The modulation performed at blocks 306, 308, and 310 is performed to generate a charge accumulation that results in current flow through the body tissues that captures and depolarizes the targeted tissue. In some examples, therapy delivery circuit 84 only modulates the high frequency oscillations of the pulse signal at block 306 (and optionally amplitude at block 308) or only modulates the low frequency bias at block 310 to generate an accumulated charge to cause depolarization of the targeted tissue. In other examples, both the frequency of oscillations of the pulse signal and the bias are modulated to produce the modulated high frequency electrical stimulation pulse signal.

The therapy delivery circuit 84 terminates the therapeutic electrical stimulation pulse at block 312 when the pulse width timer expires. The control circuit 80 may start the next stimulation interval (e.g., pacing interval) at block 314. During the stimulation interval, a charging circuit, e.g., included pulse signal source 150 in FIG. 6, may charge holding capacitors or other charge storage device(s) at block 316 to a voltage required to generate the desired maximum pulse amplitude during the next electrical stimulation pulse signal. In other examples, a battery or other medical device power source may be coupled to a voltage or current regulator of therapy delivery circuit 84 directly for producing the pulse signal, without requiring charging of a storage device at block 316 between electrical stimulation pulses.

In some examples, the type of modulation, e.g., high frequency modulation between a maximum and minimum frequency of the oscillations within the pulse signal or low frequency modulation of the bias, may be selected and programmable based on patient response. Different control parameters including, but not limited to, starting high frequency, ending high frequency, maximum frequency of oscillation, minimum frequency of oscillations, starting pulse amplitude, ending pulse amplitude, maximum pulse amplitude, pulse signal envelope or shape (determined by pulse amplitude rate of change and pulse amplitude control), total pulse width, frequency of oscillations of the bias, maximum and minimum bias offsets, rate of change of the bias, duration of holding the bias constant at a specified offset, or any combination of these modulation control parameters may be adjusted to determine a parameter value or combination of parameter values tailored to the patient that achieves capture and depolarization of the targeted tissue while minimizing patient sensation and/or discomfort caused by the electrical stimulation pulse. These various control parameters may be programmable by a user interacting with external device 40 in some examples such that any combination of high frequency modulation and/or low frequency bias modulation, with or without pulse amplitude modulation may be selected and controlled according to default or programmable control parameters.

Figure 10:
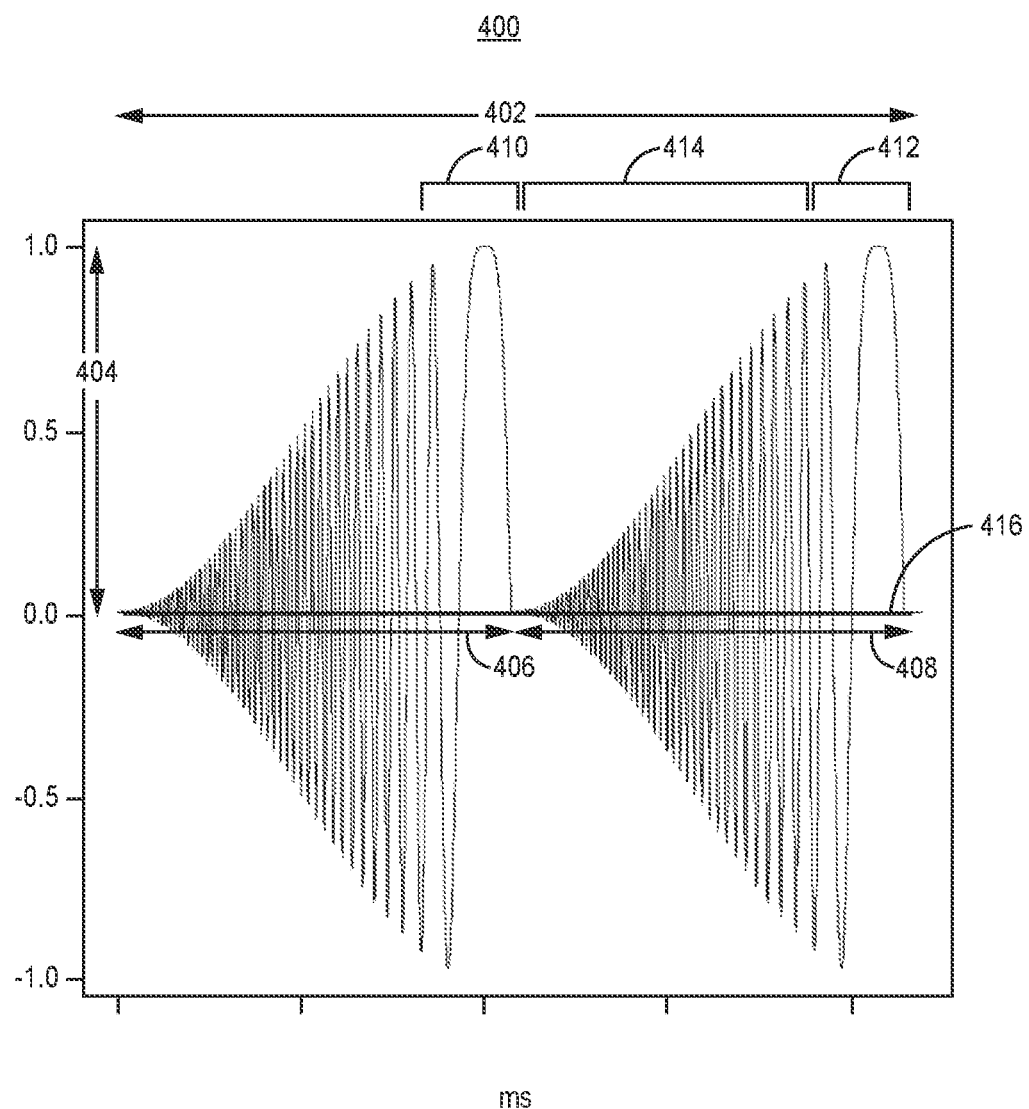
FIG. 10 is a diagram of a modulated high frequency signal that may be generated by a medical device according to another example.

FIG. 10 is a diagram of a modulated high frequency pulse signal 400 that may be generated by therapy delivery circuit 84 according to another example. In this example, the high frequency of pulse signal oscillations is decreased from a maximum, starting frequency to a minimum frequency over a modulation interval 406 as the pulse amplitude of the high frequency oscillations is increased from a minimum pulse amplitude to a maximum pulse amplitude 404. At the expiration of the modulation interval 406 and the start of the next modulation interval 408, the pulse amplitude drops to the minimum (0 Volts in the example) and the frequency makes a step increase from the minimum frequency to the maximum frequency. In this example, the high amplitude, low frequency portion 410 during modulation interval 406 may capture the myocardium (or other targeted tissue) to cause an evoked response (stimulation-induced depolarization). The frequency of the pulse signal oscillations may decrease again over the next modulation interval 408 as pulse amplitude increases to the maximum pulse amplitude 404. The next high amplitude, low frequency portion 412, at the end of the modulation interval 408, may also capture the myocardium (or other targeted tissue) causing the next evoked response. In this example, the bias 416 may be held constant by the therapy delivery circuit 84. In other examples, however, the low frequency bias generator 156 may modulate the bias 416 according to any of the examples given above to contribute to the charge accumulation during each modulation interval 406. For example, the bias 416 may be adjusted to reach a maximum offset during the low frequency, amplitude portion 410 and 412 of each modulation interval 406 and 408, respectively.

In this example, the modulation intervals 406 and 408, which determine the rate at which the low frequency, high amplitude capturing portions 410 and 412 occur, may correspond to an electrical stimulation rate interval. For example, the modulation intervals 406 and 408 may be lower pacing rate intervals, anti-tachycardia pacing intervals, or other pacing intervals set by timing circuit 90 of control circuit 80, in accordance with a pacing therapy protocol. The modulation intervals 406, 408 may be repeated consecutively with a zero millisecond delay between the end of one interval 406 and the start of the next interval 408 such that a continuous, modulated signal is delivered via a selected stimulation electrode pair with the frequency of oscillations modulated down to the minimum frequency at a rate corresponding to a pacing (or other stimulation) rate. The modulation intervals 406 and 408 may be adjusted to vary the stimulation rate. As the modulation intervals 406 and 408 are changed, e.g., to adjust pacing rate, the rate of decreasing the frequency of oscillations from the starting maximum frequency to the ending minimum frequency and the rate of increasing the pulse amplitude from the minimum to the maximum pulse amplitude may be adjusted accordingly such that a low frequency, high amplitude portion 410 and 412 of the modulation intervals 406 and 408 is defined by the minimum frequency and maximum amplitude required to achieve capture at the desired stimulation rate. In this example, the low frequency, high amplitude portions 410 and 412 are terminal portions of each modulation interval 406 and 408. However, in other examples, the low frequency, high amplitude portions 410 and 412 may occur earlier during the modulation intervals 406 and 408 such that they occur at a therapy stimulation rate interval apart from each other.

In other examples, the modulated high frequency signal 400 may correspond to a single composite electrical stimulation pulse in which the charge resulting from both of the high amplitude, low frequency portions 410 and 412 of the pulse signal 400 accumulates within a short enough time interval that the two high amplitude, low frequency portions 410 and 412 collectively cause capture of the myocardium (or other targeted tissue). In this case, the modulation intervals 406 and 408 are set such that the time interval 414 between the high amplitude, low frequency portions 410 and 412 is small enough, e.g., less than 1 ms, to result in cumulative net charge over the pulse width 402 sufficient to capture the targeted tissue. The overall pulse width 402 including two (or more) high amplitude, low frequency portions 410 and 412 may correspond to a single electrical stimulation pulse that produces a single depolarization of the targeted tissue, e.g., a single myocardial depolarization.

Figure 11:
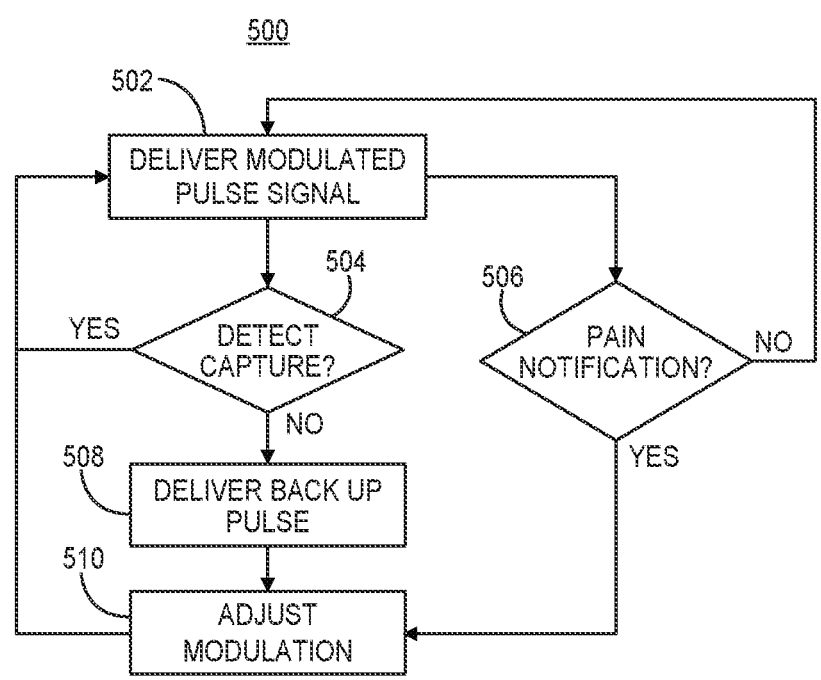
FIG. 11 is a flow chart of a method performed by a medical device for controlling a cardiac electrical stimulation therapy according to one example.

FIG. 11 is a flow chart 500 of a method performed by a medical device for controlling a cardiac electrical stimulation therapy according to one example. At block 502, a modulated high frequency pulse signal, which may correspond to any of the example modulated pulse signals described herein, is delivered according to a therapy delivery protocol, e.g., upon expiration of a specified pacing interval. As described above, the signal may be a pacing pulse that is delivered to treat tachycardia, bradycardia, asystole or as part of any other pacing protocol including tachyarrhythmia induction pacing, for example. At block 504, control circuit 80 may determine if the modulated pulse signal captured the myocardium. In some examples, capture is detected by control circuit 80 based on sensing an evoked cardiac event, e.g., sensing an R-wave by sensing circuit 86, or by detecting the evoked cardiac event signal from a digitized cardiac electrical signal received by control circuit 80 from sensing circuit 86. Control circuit 80 may detect capture from the cardiac electrical signal based on waveform morphology or other signal feature analysis. When capture is detected, no adjustment of modulation control parameters used by therapy delivery circuit 84 in generating the pulse signal is needed. Therapy delivery circuit 84 may continue generating the pulse signals at block 502 according to the current modulation control parameters that control the pulse amplitude, frequency, bias, pulse width, and other pulse features.

When capture is not detected by control circuit 80 at block 504, control circuit 80 may optionally control therapy delivery circuit 84 to generate a back-up pacing pulse at block 508 to avoid asystole. For example, control circuit 80 may control therapy delivery circuit 84 to generate a modulated high frequency signal having an increased pulse amplitude. The pulse amplitude may be set to a maximal value expected to be well above a capture threshold to ensure pacing capture with a high degree of certainty. In other examples, control circuit 80 may control therapy delivery circuit 84 to generate a standard, high amplitude pacing pulse (that is not a high frequency oscillating signal) that is expected to capture the myocardium. In this case, the patient may experience a sensation or discomfort due to the standard, high amplitude pacing pulse. However, occasional discomfort may be warranted in order to avoid heart rhythm irregularities or other symptoms.

At block 510, control circuit 80 may adjust one or more modulation control parameters in response to detecting loss of capture at block 504 (no capture detected). For instance, control circuit 80 may increase the maximum pulse amplitude or the rate of pulse amplitude increase, enable bias modulation, increase a maximum bias offset, decrease the minimum frequency reached at a time of the maximum amplitude, increase the rate of decreasing the frequency of oscillations, increase the pulse width, or any combination thereof. In some examples, adjustments of modulation control parameters at block 510 to increase the likelihood of cardiac capture may be performed in conjunction with adjustments to the modulation parameters that will also reduce the likelihood of pain or sensation caused by the adjusted pulse signal. For example, if the maximum pulse amplitude is increased, the maximum frequency and/or the shape of the maximum amplitude envelope of the pulse signal may be adjusted (e.g., by adjusting the rate of increasing or decreasing the pulse amplitude and/or increasing the duration of the first portion of the pulse width over which the frequency is decreased) to promote sensory and/or muscle nerve blocking prior to the capturing portion of the modulated pulse signal. After adjusting the modulation control parameters at block 510, therapy delivery circuit 84 may generate the next modulated pulse signal at block 502 according to the adjusted modulation control parameters.

In some examples, control circuit 80 may be configured to detect a pain notification at block 506. For example, the patient or a caregiver may transmit a signal using external device 40 to ICD 14 indicating that the patient is experiencing pain or sensation of the delivered pacing pulse signals. Telemetry circuit 88 may pass a pain notification signal to control circuit 80. In some examples, control circuit 80 may include a piezoelectric sensor or other device that responds to finger-tapping on the ICD 14 as a signal that the patient is experiencing pain or sensation of the delivered pulse signals. As long as a pain notification is not received or detected by control circuit 80 ("no" branch of block 506), therapy delivery circuit 84 may continue to generate the modulated high frequency pulse signals at block 502 according to current modulation control parameters. When control circuit 80 receives a pain notification signal at block 506, control circuit 80 may adjust modulation control parameters of block 510, regardless of capture detection occurring at block 504.

At block 510, control circuit 80 may increase or decrease the maximum frequency of the modulated pulse signal, adjust the amplitude modulation to increase the amplitude of the higher frequency portion(s) of the pulse signal, and/or decrease the maximum amplitude of the low frequency portion(s) of the pulse signal. In some examples, control circuit 80 may adjust the modulation control parameters at block 510 to promote a reduction in pain or sensation and to promote capture at the adjusted modulation control parameters. For example, if the maximum pulse amplitude is decreased to reduce the likelihood of pain or sensation, control circuit 80 may add bias modulation, increase a maximum offset of bias modulation or number of bias modulation oscillations, and/or decrease a minimum frequency of the frequency modulation that coincides with the maximum pulse amplitude to increase the charge accumulation during the high pulse amplitude portion of the pulse signal to promote capture. After adjusting the modulation control parameters, therapy delivery circuit 84 may generate the next modulated pulse signal at block 502 according to the adjusted parameters.

In the example of FIG. 11, control circuit 80 is configured to adjust modulation control parameters in response to both a loss of capture detection and a pain notification detection. It is to be understood that in other examples control circuit 80 may be configured to detect capture and adjust modulation control parameters to increase the likelihood of capture in response to a loss of capture detection without being configured to detect a pain notification. In other examples, control circuit 80 may be configured to detect a pain notification and adjust modulation control parameters to reduce the likelihood of pain or sensation caused by delivery of the modulated high frequency pulse signals without necessarily being configured to detect capture. In each of these examples, it is understood that the modulation adjustments may be limited to within a predetermined range of available settings to minimize the likelihood of loss of capture and/or increased pain or sensation.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units or circuits associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPLAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a medical device has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A medical device system comprising a medical device, the medical device including a therapy delivery circuit configured to:
generate an electrical stimulation pulse signal that oscillates throughout a pulse width;
modulate the oscillations of the stimulation pulse signal between at least one of:
a maximum frequency and a minimum frequency that is different than the maximum frequency; or
a maximum offset and a minimum offset of a bias of the electrical stimulation pulse signal, the minimum offset being different than the maximum offset; and
modulate an amplitude of the electrical stimulation pulse signal between a minimum amplitude and maximum amplitude during the pulse width so that the maximum amplitude is at a time during the pulse width of at least one of:
the minimum frequency of the oscillations of the stimulation pulse signal; or
the maximum offset of the bias of the electrical stimulation pulse signal; and
deliver the modulated electrical stimulation pulse signal to a stimulation electrode.

2. The medical device system of claim 1 wherein the therapy delivery circuit is further configured to modulate the electrical stimulation pulse signal by:
modulating the oscillations of the electrical stimulation pulse signal between the maximum frequency and the minimum frequency during the pulse width; and
modulating the amplitude of the electrical stimulation pulse signal from the minimum amplitude to the maximum amplitude coinciding with the time during the pulse width of the minimum frequency.

3. The medical device system of claim 1 wherein the therapy delivery circuit is further configured to modulate the electrical stimulation pulse signal to have the maximum amplitude at the time during the pulse width by:
modulating the bias of the electrical stimulation pulse signal between the minimum offset and the maximum offset; and
modulating the amplitude of the electrical stimulation pulse signal from the minimum amplitude to the maximum amplitude coinciding with the time during the pulse width of the maximum offset of the bias.

4. The medical device system of claim 1 wherein the therapy delivery circuit is further configured to modulate the electrical stimulation pulse signal to have the maximum amplitude at the time during the pulse width by modulating the bias of the electrical stimulation pulse signal between the minimum offset and the maximum offset without modulating the frequency of the oscillations of the stimulation pulse signal.

5. The medical device system of claim 1 wherein the therapy delivery circuit is further configured to:
modulate the bias between the minimum offset and the maximum offset at a first rate; and
modulate the amplitude of the electrical stimulation pulse signal between the minimum amplitude and the maximum amplitude at a second rate different than the first rate.

6. The medical device system of claim 1, wherein the medical device further comprises:
a cardiac sensing circuit configured to sense a cardiac signal;
a control circuit configured to:
detect loss of capture following the electrical stimulation pulse signal based on the sensed cardiac signal; and
in response to detecting the loss of capture, adjust at least a first modulation control parameter to promote cardiac capture by adjusting at least one of:
the maximum amplitude;
a rate of increasing the amplitude of the electrical stimulation pulse signal to the maximum amplitude;
the maximum offset of the bias;
the minimum frequency of the oscillations;
a rate of decreasing a frequency of the oscillations to the minimum frequency; or
the pulse width; and
the therapy delivery circuit further configured to generate a next electrical stimulation pulse signal according to at least the adjusted first modulation control parameter.

7. The medical device system of claim 6 wherein the control circuit is further configured to adjust a second modulation control parameter to promote a reduced sensation of the next electrical stimulation pulse signal by adjusting at least one of:
the maximum frequency of the oscillations;
a rate of increasing an amplitude of the next electrical stimulation pulse signal to the maximum amplitude; or
a rate of decreasing a frequency of the oscillations of the next electrical stimulation pulse signal to the minimum frequency.

8. The medical device system of claim 1, wherein the medical device further comprises:
a cardiac sensing circuit configured to sense a cardiac signal;
a control circuit configured to:
detect loss of capture following the electrical stimulation pulse signal based on the sensed cardiac signal; and
in response to detecting the loss of capture, control the therapy delivery circuit to deliver a back up pacing pulse that is not an oscillating signal.

9. The medical device system of claim 1, wherein the medical device further comprises:
a control circuit configured to:
start a cardiac pacing interval; and
detect an expiration of the cardiac pacing interval;
wherein the therapy delivery circuit is configured to generate the electrical stimulation pulse signal in response to the cardiac pacing interval expiring.

10. The medical device system of claim 1, wherein the medical device further comprises:
a cardiac sensing circuit configured to sense a cardiac signal;
a control circuit configured to detect a tachyarrhythmia based on the cardiac signal; and
wherein the therapy delivery circuit is configured to generate the electrical stimulation pulse signal in response to the control circuit detecting the tachyarrhythmia.

11. The medical device system of claim 1, further comprising a medical electrical lead carrying the stimulation electrode, the medical electrical lead couplable to the medical device.

12. A method including:
generating an electrical stimulation pulse signal that oscillates throughout a pulse width;
modulating the oscillations of the stimulation pulse signal being between at least one of:
a maximum frequency and a minimum frequency that is different than the maximum frequency; or
a maximum offset and a minimum offset of a bias of the electrical stimulation pulse signal, the minimum offset being different than the maximum offset;
modulating an amplitude of the electrical stimulation pulse signal between a minimum amplitude and a maximum amplitude during the pulse width so that the maximum amplitude is at a time during the pulse width of at least one of:
the minimum frequency of the oscillations of the stimulation pulse signal; or
the maximum offset of the bias of the electrical stimulation pulse signal; and
delivering the modulated electrical stimulation pulse signal to a stimulation electrode.

13. The method of claim 12 wherein modulating the electrical stimulation pulse signal further comprises:
modulating the oscillations of the electrical stimulation pulse signal between the maximum frequency and the minimum frequency during the pulse width; and
modulating the amplitude of the electrical stimulation pulse signal from the minimum amplitude to the maximum amplitude coinciding with the time during the pulse width of the minimum frequency.

14. The method of claim 12 wherein modulating the electrical stimulation pulse signal to have the maximum amplitude at the time during the pulse width further comprises:
modulating the bias of the electrical stimulation pulse signal between the minimum offset and the maximum offset; and
modulating an amplitude of the electrical stimulation pulse signal from the minimum amplitude to the maximum amplitude coinciding with the time during the pulse width of the maximum offset of the bias.

15. The method of claim 12 wherein modulating the electrical stimulation pulse signal to have the maximum amplitude at the time during the pulse width further comprises modulating the bias of the electrical stimulation pulse signal between the minimum offset and the maximum offset without modulating the frequency of the oscillations of the stimulation pulse signal.

16. The method of claim 12 further comprising:
modulating the bias between the minimum offset and the maximum offset at a first rate; and
modulating the amplitude of the electrical stimulation pulse signal between the minimum amplitude and the maximum amplitude at a second rate different than the first rate.

17. The method of claim 12 further comprising:
sensing a cardiac signal;
detecting loss of capture following the electrical stimulation pulse signal based on the sensed cardiac signal; and
in response to detecting the loss of capture, adjusting at least a first modulation control parameter to promote cardiac capture by adjusting at least one of:
the maximum amplitude;
a rate of increasing the amplitude of the electrical stimulation pulse signal to the maximum amplitude;
the maximum offset of the bias;
the minimum frequency of the oscillations;
a rate of decreasing a frequency of the oscillations to the minimum frequency; or
the pulse width; and
generating a next electrical stimulation pulse signal according to at least the adjusted first modulation control parameter.

18. The method of claim 17 further comprising adjusting a second modulation control parameter to promote a reduced sensation of the next electrical stimulation pulse signal by adjusting at least one of:
the maximum frequency of the oscillations;
a rate of increasing an amplitude of the next electrical stimulation pulse signal to the maximum amplitude; or
a rate of decreasing a frequency of the oscillations of the next electrical stimulation pulse signal to the minimum frequency.

19. The method of claim 12 further comprising:
sensing a cardiac signal;
detecting loss of capture following the electrical stimulation pulse signal based on the sensed cardiac signal; and
in response to detecting the loss of capture, delivering a back up pacing pulse that is not an oscillating signal.

20. The method of claim 12, further comprising:
starting a cardiac pacing interval;
detecting an expiration of the cardiac pacing interval; and
generating the electrical stimulation pulse signal in response to the cardiac pacing interval expiring.

21. The method of claim 12, further comprising:
sensing a cardiac signal;
detecting a tachyarrhythmia based on the cardiac signal; and
generating the electrical stimulation pulse signal in response to detecting the tachyarrhythmia.

* * * * *